(12) United States Patent
Igarashi

(10) Patent No.: US 12,319,008 B2
(45) Date of Patent: Jun. 3, 2025

(54) FLOW PATH SEALING STRUCTURE, BAG-SHAPED CONTAINER, AND METHOD OF MANUFACTURING THE SAME

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 507 days.

(21) Appl. No.: 17/697,602

(22) Filed: Mar. 17, 2022

(65) Prior Publication Data

US 2022/0203628 A1 Jun. 30, 2022

Related U.S. Application Data

(63) Continuation of application No. PCT/JP2020/034035, filed on Sep. 9, 2020.

(30) Foreign Application Priority Data

Sep. 19, 2019 (JP) .................................. 2019-170097

(51) Int. Cl.
*B29C 65/76* (2006.01)
*A61J 1/12* (2006.01)
(Continued)

(52) U.S. Cl.
CPC ................. *B29C 65/76* (2013.01); *A61J 1/12* (2013.01); *A61J 1/1412* (2013.01); *A61J 1/2024* (2015.05);
(Continued)

(58) Field of Classification Search
CPC .......... A61J 1/20; A61J 1/2003; A61J 1/2024; A61J 1/1468; B29C 65/76
See application file for complete search history.

(56) References Cited

U.S. PATENT DOCUMENTS

2008/0262408 A1 10/2008 Krauss et al.
2009/0254032 A1 10/2009 Muramatsu

FOREIGN PATENT DOCUMENTS

DE 202005004135 5/2005
JP H06-105890 4/1994
(Continued)

OTHER PUBLICATIONS

Machine Translation JP200604345.*
(Continued)

*Primary Examiner* — Christopher T Schatz
(74) *Attorney, Agent, or Firm* — Sheridan Ross P.C.

(57) ABSTRACT

A flow path sealing structure according to at least one embodiment of the present disclosure, which is disposed on a way of a flow path formed by fusion bonding a pair of resin sheets that are superimposed on each other, includes a widened portion surrounded by a widened seal portion formed by fusion bonding together the pair of resin sheets around a periphery thereof, and one end and another end of which are in communication with the flow path, together with being formed to be wider than the flow path, and a weakly sealed portion formed to extend in a widthwise direction in the widened portion, and which partitions the widened portion in a liquid-tight and airtight manner into the one end and the other end, together with being capable of being opened by increasing an internal pressure of the widened portion.

11 Claims, 13 Drawing Sheets

(51) Int. Cl.
    *A61J 1/14*            (2023.01)
    *A61J 1/20*            (2006.01)
    *B29C 65/00*          (2006.01)
    *B29C 65/04*          (2006.01)
    *B29C 65/82*          (2006.01)
    *B29L 31/00*          (2006.01)

(52) U.S. Cl.
    CPC .......... *B29C 65/04* (2013.01); *B29C 65/8246* (2013.01); *B29C 66/1122* (2013.01); *B29C 66/244* (2013.01); *B29C 66/3452* (2013.01); *B29C 66/3472* (2013.01); *B29C 66/43121* (2013.01); *B29C 66/71* (2013.01); *B29C 66/73921* (2013.01); *B29C 66/81427* (2013.01); *B29C 66/8322* (2013.01); *B29C 66/91423* (2013.01); *B29C 66/9161* (2013.01); *B29L 2031/7148* (2013.01)

(56) References Cited

FOREIGN PATENT DOCUMENTS

| | | |
|---|---|---|
| JP | 2006-043405 | 2/2006 |
| JP | 2007-151844 | 6/2007 |
| JP | 2019-170097 | 10/2019 |
| WO | WO 2012/175436 | 12/2012 |

OTHER PUBLICATIONS

International Search Report and Written Opinion for International (PCT) Patent Application No. PCT/JP2020/034035, dated Dec. 8, 2020, 11 pages.

Official Action (with English translation) for Japan Patent Application No. 2022-508768, dated Aug. 29, 2023, 14 pages.

\* cited by examiner

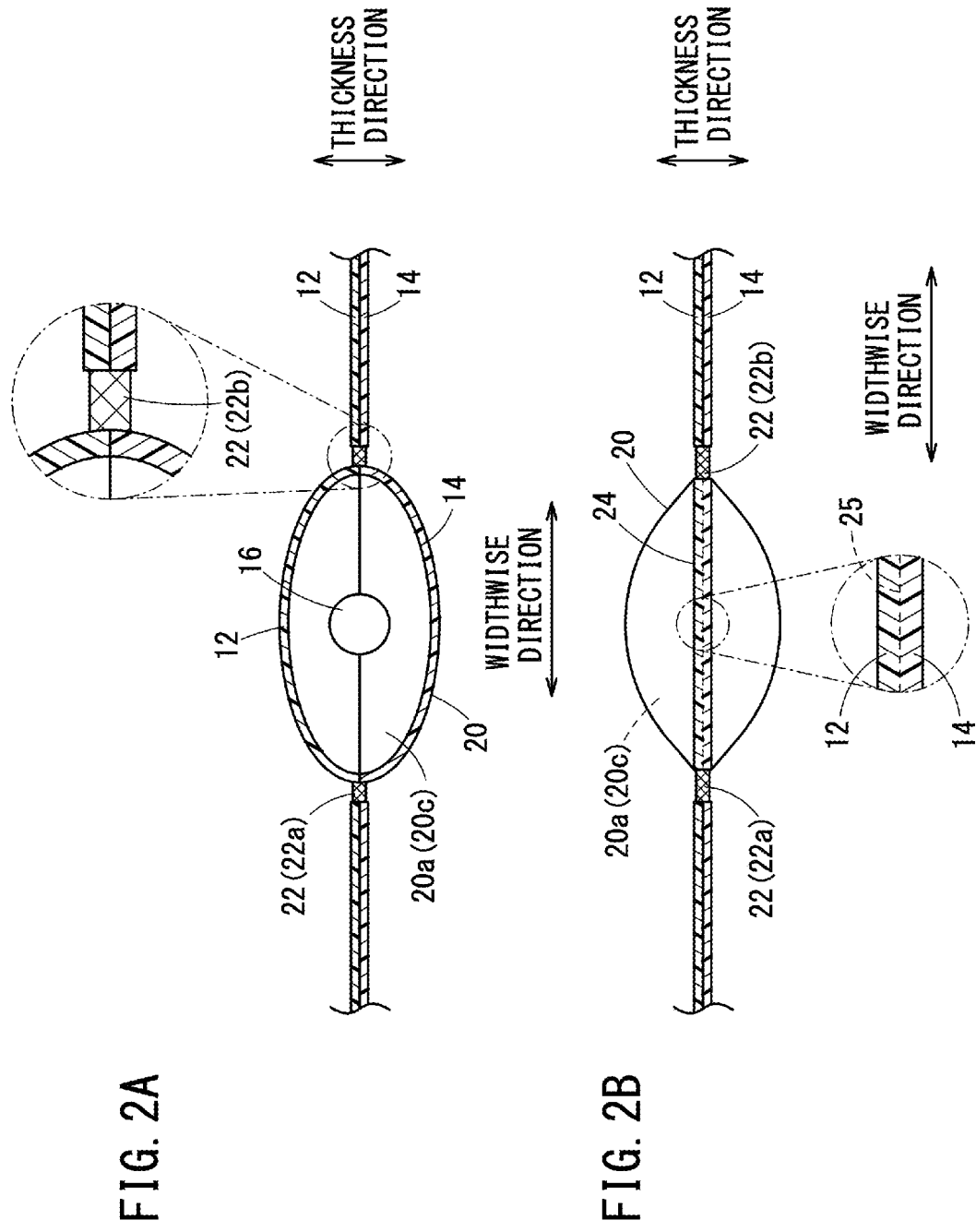

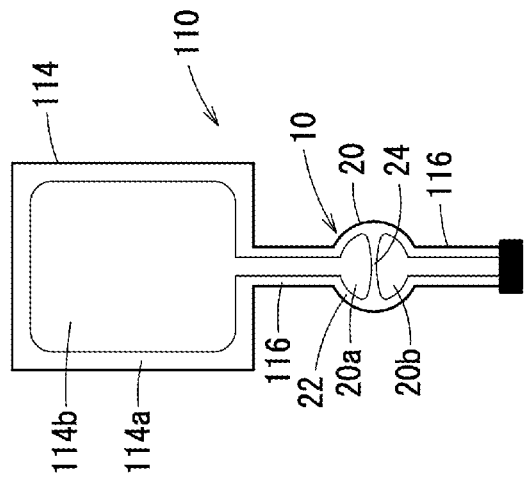
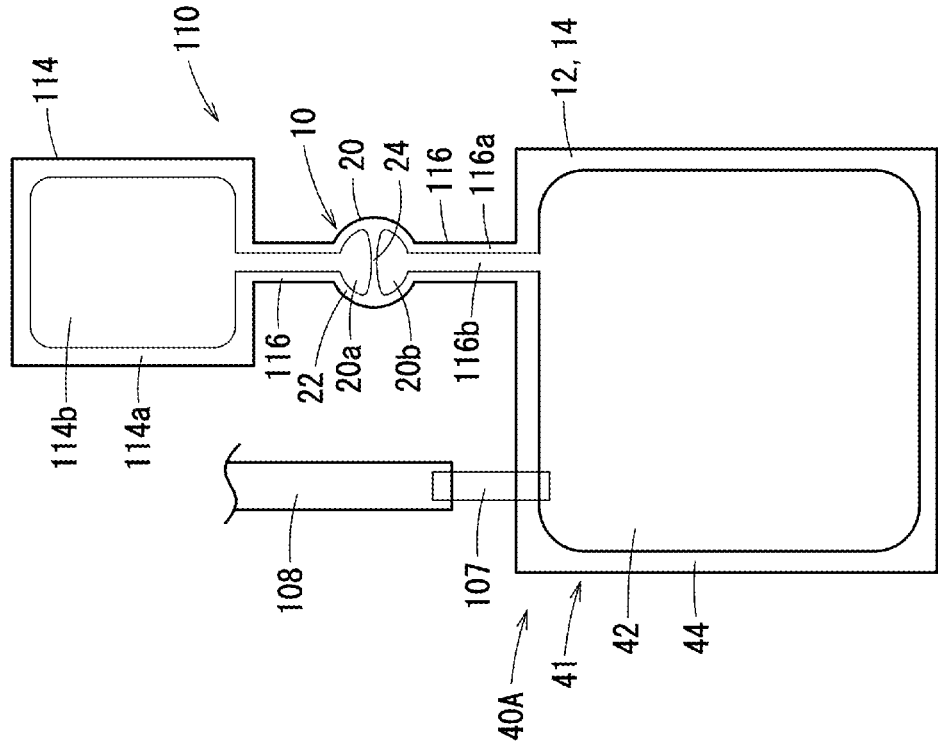

FLOW PATH SEALING STRUCTURE, BAG-SHAPED CONTAINER, AND METHOD OF MANUFACTURING THE SAME

CROSS REFERENCE TO RELATED APPLICATIONS

The present disclosure is a continuation of and claims benefit to PCT Application No. PCT/JP2020/034035 filed on Sep. 9, 2020, entitled "FLOW PATH SEALING STRUCTURE, BAG-SHAPED CONTAINER, AND METHOD OF MANUFACTURING THE SAME" which claims priority to Japanese Patent Application No. 2019-170097 filed on Sep. 19, 2019. The entire disclosure of the applications listed above are hereby incorporated herein by reference, in their entirety, for all that they teach and for all purposes.

BACKGROUND

The present disclosure relates to a flow path sealing structure for sealing a flow path formed by fusion bonding resin sheets, a bag-shaped container, and a method of manufacturing the same.

Various bag-shaped containers formed by fusion bonding resin sheets have been proposed. For example, in Japanese Laid-Open Patent Publication No. 06-105890, a blood collection bag in the form of a bag-shaped container is disclosed. In such a bag-shaped container, there are cases in which a flow path for injection or removal of contents is connected to the bag-shaped container, and in such a flow path, a sealing member is provided in order to seal the bag-shaped container.

In Japanese Laid-Open Patent Publication No. 06-105890, a flow path sealing member is disclosed in which a breakable closing member is provided in the interior of a tubular member that possesses flexibility. The flow path sealing member can be opened by a user bending the tubular member and causing the closing member to break.

SUMMARY

Since such a conventional flow path sealing member is composed of a plurality of component parts, a process of assembling the plurality of component parts is required. Further, a step of fusion bonding the flow path sealing structure to the bag-shaped container is required. Therefore, in the case that such a conventional flow path sealing member is provided in the flow path, a problem arises in that manufacturing costs are increased.

As a method of suppressing manufacturing costs, it may be considered to form the bag-shaped container and the flow path integrally by fusion bonding a pair of resin sheets, together with providing a weakly sealed portion on the flow path to thereby integrally form the flow path sealing member with the resin sheets.

However, it is difficult to control the sealing strength of the weakly sealed portion, and even if manufactured under the same conditions, it has been ascertained that there is a possibility that defective products may be produced in which leakage of fluid occurs due to the sealing strength being insufficient, or in which the sealing strength is too strong and the flow path sealing member cannot be opened.

One aspect of the present disclosure has an object of providing, for example, a flow path sealing structure, a bag-shaped container, and a method of manufacturing the same, in which it is possible to reduce manufacturing costs, and to achieve stable product quality.

In some examples, a flow path sealing structure is provided, which is disposed on a way of a flow path formed by fusion bonding a pair of resin sheets that are superimposed on each other, the flow path sealing structure including a widened portion surrounded by a widened seal portion formed by fusion bonding the pair of resin sheets around a periphery thereof, and one end and another end of which are in communication with the flow path, the widened portion being formed to be wider than the flow path, and a weakly sealed portion formed to extend in a widthwise direction in the widened portion, and which partitions the widened portion in a liquid-tight and airtight manner into a first region on a side of the one end and a second region on a side of the other end, the weakly sealed portion configured to be opened by increasing an internal pressure of the widened portion.

Another aspect of the present disclosure is a bag-shaped container which is provided with the flow path sealing structure according to the above-described aspect.

A still further aspect of the present disclosure is a method of manufacturing a flow path sealing structure, including a step of superimposing a pair of resin sheets in a thickness direction, a first fusion bonding step of fusion bonding the pair of resin sheets to thereby form a flow path, and a widened portion disposed on a way of the flow path and which is formed to be wider than the flow path, and a second fusion bonding step of fusion bonding the resin sheets of the widened portion to thereby form a weakly sealed portion that crosses in a widthwise direction, wherein, in the second fusion bonding step, fusion bonding is carried out under a condition in which an amount of input heat per unit area is less than in the first fusion bonding step.

A still further aspect of the present disclosure is a method of manufacturing a bag-shaped container, including a step of superimposing a pair of resin sheets in a thickness direction, a first fusion bonding step of fusion bonding the pair of resin sheets to thereby form an accommodating section, a flow path, and a widened portion disposed on a way of the flow path and which is formed to be wider than the flow path, and a second fusion bonding step of fusion bonding the resin sheets of the widened portion to thereby form a weakly sealed portion that crosses in a widthwise direction, wherein, in the second fusion bonding step, fusion bonding is carried out under a condition in which an amount of input heat per unit area is less than in the first fusion bonding step.

A still further aspect of the present disclosure is a blood bag system, including a blood collection bag in which whole blood is collected, a parent bag in which centrifugal separation of the whole blood is carried out, a child bag in which a portion of a separated blood component is accommodated, a medicinal solution bag in which a storage solution for the blood component is accommodated, a first flow path configured to connect the blood collection bag and the parent bag, and a second flow path configured to connect the parent bag, the child bag, and the medicinal solution bag, wherein the blood collection bag, the parent bag, the child bag, the medicinal solution bag, the first flow path, and the second flow path are integrally formed by fusion bonding a pair of resin sheets, and there is provided a flow path sealing structure disposed in at least one of the paths of the first flow path and the second flow path, the flow path sealing structure including a widened portion surrounded by a widened seal portion formed by fusion bonding the pair of resin sheets around a periphery thereof, and one end and another end of which are in communication with the flow path, the widened portion being formed to be wider than the flow path, and a weakly sealed portion formed to extend in a widthwise direction in the widened portion, and which partitions the widened portion in a liquid-tight and airtight manner into a first region on a side of the one end and a second region on a side of the other end, the weakly sealed portion configured to be opened by increasing an internal pressure of the widened portion.

A still further aspect of the present disclosure is a sample collecting structure for a bag-shaped container, including a flow path connected to the bag-shaped container in which an accommodating section is formed in an interior thereof, and which is placed in communication with the accommodating section, a sample container connected to the bag-shaped container via the flow path, and a flow path sealing structure disposed on a way of the flow path and configured to seal the flow path, wherein the flow path, the sample container, and the flow path sealing structure are formed integrally with the bag-shaped container by fusion bonding a pair of resin sheets, the flow path sealing structure including a widened portion surrounded by a widened seal portion formed by fusion bonding the pair of resin sheets around a periphery thereof, and one end and another end of which are in communication with the flow path, the widened portion being formed to be wider than the flow path, and a weakly sealed portion formed to extend in a widthwise direction in the widened portion, and which partitions the widened portion in a liquid-tight and airtight manner into a first region on a side of the one end and a second region on a side of the other end, the weakly sealed portion configured to be opened by increasing an internal pressure of the widened portion.

Among other things, the flow path sealing structure, the bag-shaped container, and the method of manufacturing the same according to the above-described examples and aspects are capable of reducing manufacturing cost and bringing about stable product quality.

BRIEF DESCRIPTION OF THE DRAWINGS

FIG. 2A is a cross-sectional view taken along line IIA-IIA of FIG. 1A according to embodiments of the present disclosure;

FIG. 2B is a cross-sectional view taken along line IIB-IIB of FIG. 1A according to embodiments of the present disclosure;

FIG. 12A is a plan view of a bag-shaped container according to embodiments of the present disclosure;

FIG. 12B is a plan view showing a state in which a sample collecting structure shown in FIG. 12A is separated from the bag-shaped container according to embodiments of the present disclosure.

DETAILED DESCRIPTION

Figure 1A:
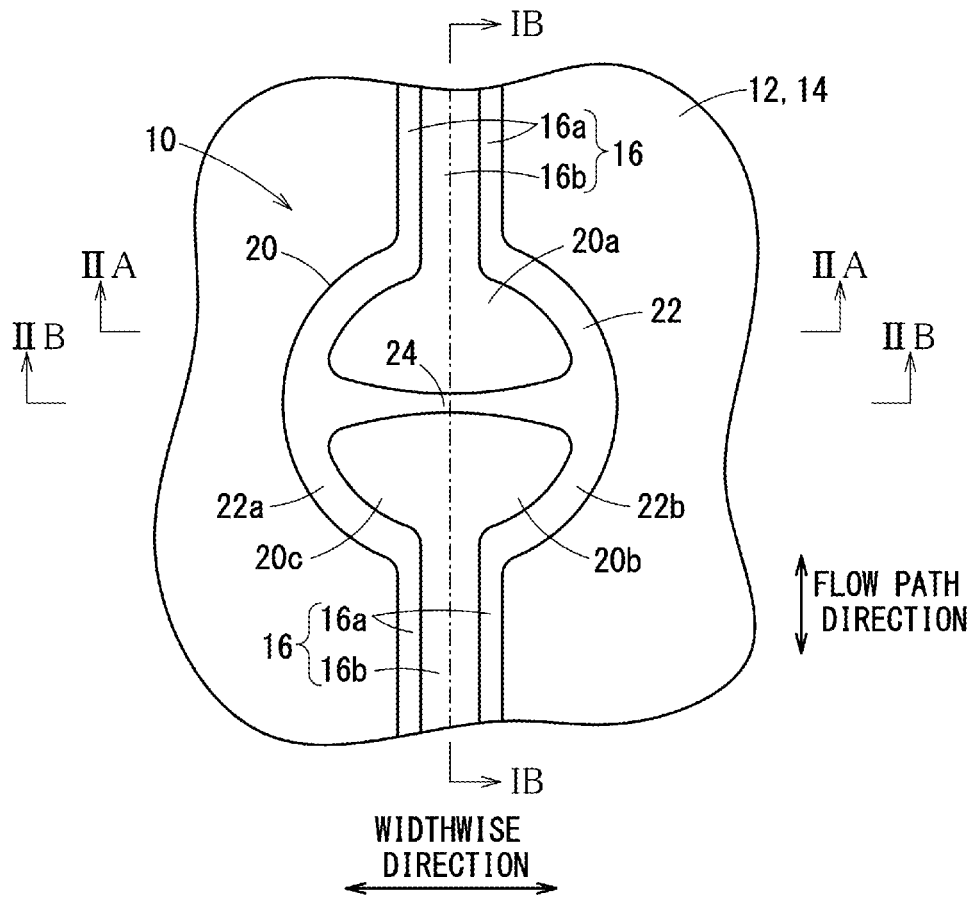
FIG. 1A is a plan view of a flow path sealing structure according to embodiments of the present disclosure.

Embodiments of the present disclosure will be presented and described in detail below with reference to the accompanying drawings. Moreover, in the present specification, a direction along a center line of the flow path is referred to as a flow path direction, whereas a direction perpendicular to such a direction is referred to as a widthwise direction of such a portion.

A flow path sealing structure 10 according to the embodiments of the present disclosure is disposed on the way of flow paths 16, which are obtained by superimposing a pair of resin sheets 12 and 14 on each other and subjecting them to fusion bonding, and is formed integrally with the flow paths 16 by the resin sheets 12 and 14. The flow path sealing structure 10 seals the flow paths 16 so that they are capable of being opened at a weakly sealed portion 24, and is maintained in a state in which the flow paths 16 are sealed in an initial state. The flow path sealing structure 10 can be opened by sending a pressurized fluid into the flow path sealing structure 10 via one or both of the flow paths 16. Such a flow path sealing structure 10 is used in connection with the flow paths, for example, of a medicinal solution bag, or a blood bag system or the like.

The resin sheets 12 and 14 that constitute the flow paths 16 and the flow path sealing structure 10 are constituted by a thermoplastic resin that is soft and possesses flexibility, such as polyvinyl chloride resin, polyurethane resin, EVA (e.g., ethylene-vinyl acetate copolymer) resin, or the like. The resin sheets 12 and 14 are superimposed on each other in a thickness direction.

The flow paths 16 include flow path sealed portions 16a and flow through portions 16b formed between the flow path sealed portions 16a. The flow path sealed portions 16a form both side portions of the flow paths 16 and extend along the flow paths 16. The flow path sealed portions 16a are constituted by a strong seal in which the resin sheets 12 and 14 are completely fusion bonded. The strong seal is a seal of a state in which an interface 25 between the two resin sheets 12 and 14 has completely disappeared. The dimension of the flow path sealed portions 16a in a widthwise direction perpendicular to a center line of the flow paths 16 is set, for example, on the order of 0.5 mm to 3 mm.

Both sides of the flow through portions 16b of the flow paths 16 are sealed by the flow path sealed portions 16a, and are sealed by the resin sheets 12 and 14 in the thickness direction. As shown in FIG. 1B, the resin sheets 12 and 14 of the flow through portions 16b are shaped so as to bulge out apart from each other in the thickness direction. The width of the flow through portions 16b can be appropriately set according to the desired flow rate, and can be formed, for example, on the order of 1 mm to 10 mm.

Figure 1B:
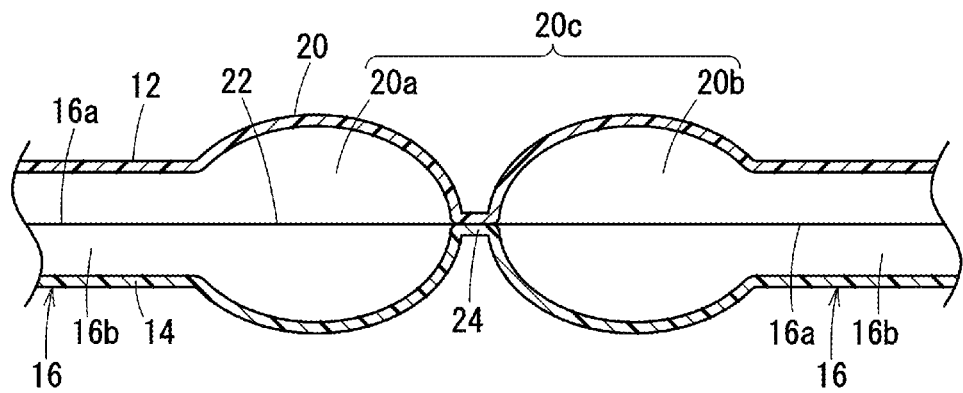
FIG. 1B is a cross-sectional view taken along line IB-IB of FIG. 1A according to embodiments of the present disclosure.

As shown in FIG. 1A, the flow path sealing structure 10 is provided on the way of the flow path 16, and is equipped with a widened portion 20 that is wider than the flow paths 16 in the widthwise direction (e.g., a direction perpendicular to the flow path direction and the thickness direction of the resin sheets 12 and 14), and a weakly sealed portion 24 that is formed across the widened portion 20. Although the thickness of the widened portion 20 is substantially the same as the thickness of the flow paths 16, the thickness thereof is not limited to this feature. The widened portion 20 may be formed to be enlarged in the thickness direction of the flow paths 16 by locally changing the direction of the fusion bonded pattern in the vicinity of the widened portion 20. The widened portion 20 is formed in a circular shape as viewed in plan, and a widened seal portion 22 is formed along the peripheral edge part thereof.

As shown in FIG. 2A, the widened seal portion 22 is constituted by a strong seal in which the resin sheets 12 and 14 are completely fusion bonded together. The widened seal portion 22 includes a semicircular arcuate portion 22a that constitutes one side portion, and a semicircular arcuate portion 22b that constitutes another side portion. The arcuate portion 22a is connected to one of the flow path sealed portions 16a of the flow paths 16. Further, the arcuate portion 22b is connected to another one of the flow path sealed portions 16a of the flow paths 16. The width of the widened seal portion 22 itself may be approximately the same as the width of the flow path sealed portions 16a.

As shown in FIG. 1A, a circular interior part 20c is formed at a portion surrounded by the widened seal portion 22. As shown in FIGS. 1B and 2A, the interior part 20c is covered with the resin sheets 12 and 14 in the thickness direction. The resin sheets 12 and 14 bulge in a manner so as to separate away from each other in the thickness direction, and form a hollow portion or cavity. The interior part 20c communicates with the flow paths 16 at one end and another end thereof in the flow path direction.

As shown in FIGS. 1A and 1B, the interior part 20c is partitioned by the weakly sealed portion 24 in a liquid-tight and airtight manner into a first region 20a and a second region 20b. The first region 20a communicates with the flow path 16 on one end side in the flow path direction, and the second region 20b communicates with the flow path 16 on the other end side. As shown in FIG. 1A, the weakly sealed portion 24 is provided in close proximity to the center of the widened portion 20 in the flow path direction, and is formed across the widened portion 20 in the widthwise direction.

The weakly sealed portion 24 is formed by fusion bonding the resin sheets 12 and 14, and as shown in FIG. 2B, the two resin sheets 12 and 14, which are superimposed on each other in the thickness direction, are fusion bonded in a state with an interface 25 left remaining therebetween. As will be described later, the weakly sealed portion 24 can be formed by being carried out under a condition in which the amount of input heat per unit area (e.g., sealing power) when the resin sheets 12 and 14 are fusion bonded is less than the amount of input heat per unit area when the strong seal is fusion bonded.

As shown in FIG. 1A, the dimension of the weakly sealed portion 24 in the flow path direction (e.g., the vertical width in the drawing) is formed to be less than the width of the widened seal portion 22 or the flow path sealed portions 16a. More preferably, the weakly sealed portion 24 may have a concavely curved shape as viewed in plan, so that a dimension thereof in the flow path direction becomes smaller toward the center in the widthwise direction. Moreover, the weakly sealed portion 24 is not limited to being arranged in a direction perpendicular to the flow path direction, and may be inclined with respect to the flow path direction.

The flow path sealing structure 10 according to embodiments of the present disclosure is constituted in the manner described above. Next, operations thereof will be described below.

The flow path sealing structure 10 is disposed on the way of the flow paths 16, and in an initial state, the weakly sealed portion 24 partitions one and another one of the flow paths 16 in a liquid-tight and airtight manner, whereby a fluid such as the medicinal solution and blood or the like is prevented from flowing.

Further, the flow path sealing structure 10 can be opened by supplying a pressurized fluid to the flow path sealing structure 10 through a bag-shaped container 40 or a pump that is connected to the flow paths 16. At that time, by the pressurized fluid flowing into the widened portion 20, the resin sheets 12 and 14 shown in FIG. 1B are pushed and spread apart in the thickness direction. As a result, at the weakly sealed portion 24, the interface 25 (see, e.g., FIG. 2B) between the resin sheets 12 and 14 is displaced in a manner so as to be peeled apart, and the flow path sealing structure 10 is opened.

Next, a description will be given concerning a method of manufacturing the flow path sealing structure 10 according to embodiments of the present disclosure.

Figure 3:
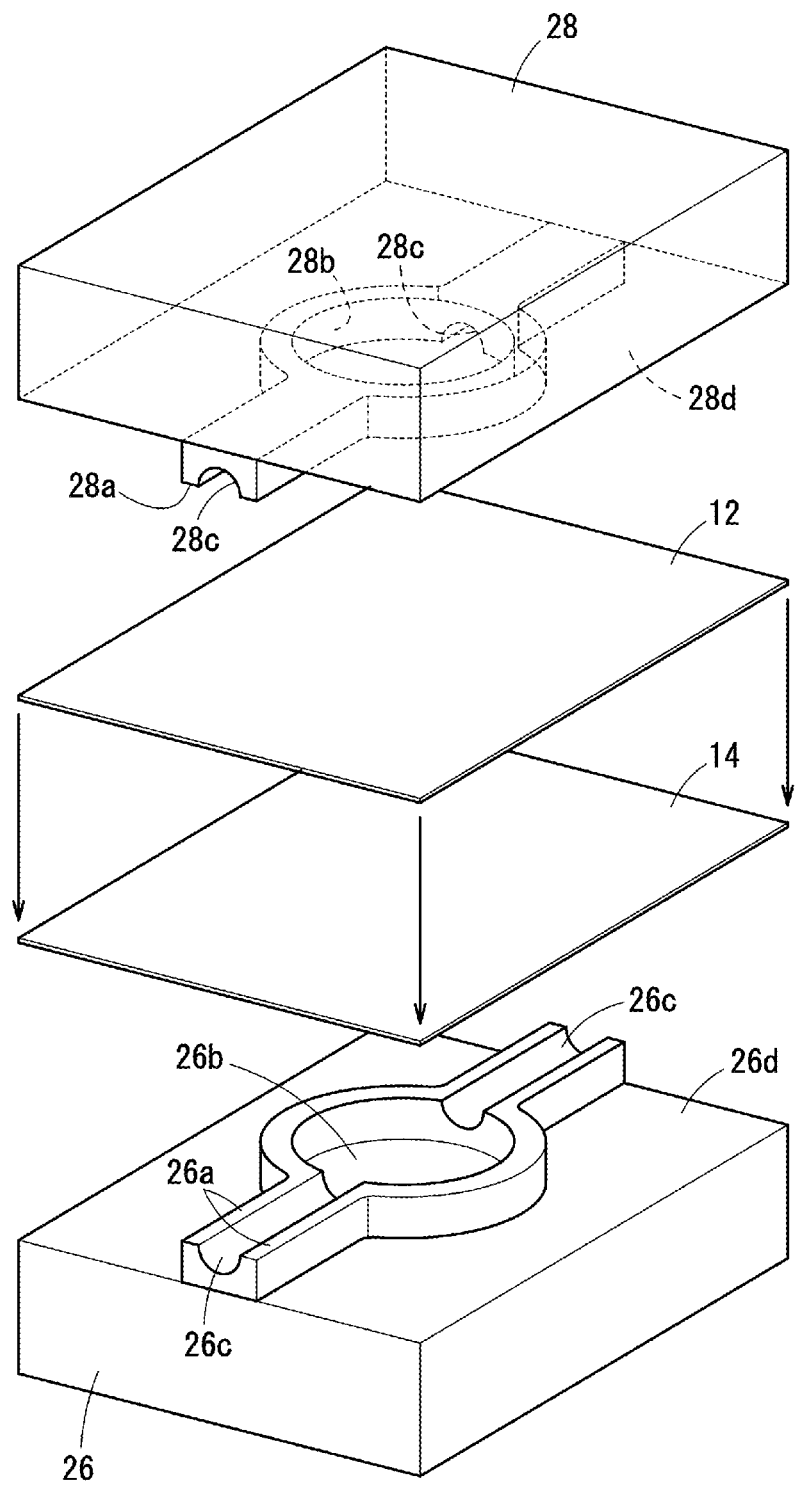
FIG. 3 is a schematic diagram showing a first fusion bonding step in a method of manufacturing the flow path sealing structure shown in FIG. 1A according to embodiments of the present disclosure.

The flow path sealing structure 10 according to embodiments of the present disclosure is manufactured by a two-step fusion bonding process with differing amounts of input heat. More specifically, the flow path sealed portions 16a and the widened seal portion 22 are formed in the first fusion bonding step, and the weakly sealed portion 24 is formed in the second fusion bonding step. Prior to the first fusion bonding step, as shown in FIG. 3, the resin sheet 12 and the resin sheet 14 are superimposed on each other in the thickness direction. In addition, the superimposed resin sheets 12 and 14 are transported inwardly between a lower mold 26 and an upper mold 28.

The lower mold 26 includes pressing parts 26a that protrude from a main surface 26d, and cavities 26b and 26c formed between the pressing parts 26a. The pressing parts 26a are formed at a portion corresponding to the flow path sealed portions 16a of the flow paths 16, and the widened seal portion 22 of the widened portion 20. The cavity 26b is provided in a portion corresponding to the interior part 20c of the widened portion 20, and is formed in a recessed (e.g., concave) cylindrical shape. The cavity 26c is provided in a portion corresponding to the flow through portions 16b of the flow paths 16, and has a cross-section that is formed in a recessed (e.g., concave) arcuate shape.

The upper mold 28 is formed vertically symmetrical with the lower mold 26, and includes pressing parts 28a that protrude from a main surface 28d, and cavities 28b and 28c formed between the pressing parts 28a. The pressing parts 28a are disposed in a portion of the lower mold 26 that faces toward the pressing parts 26a. Further, the cavities 28b and 28c are disposed in portions of the lower mold 26 that face respectively toward the cavities 26b and 26c.

Next, the lower mold 26 and the upper mold 28 press the pair of resin sheets 12 and 14. Consequently, portions of the resin sheets 12 and 14 that are sandwiched between the pressing parts 26a of the lower mold 26 and the pressing parts 28a of the upper mold 28 are placed in close contact with each other. Thereafter, pressurized air is injected between the resin sheets 12 and 14 and into the portion surrounded by the pressing parts 26a and 28a. Consequently, the resin sheet 12 bulges toward the cavities 28b, 28c of the upper mold 28. Further, the resin sheet 14 bulges toward the cavities 26b, 26c of the lower mold 26.

Figure 4:
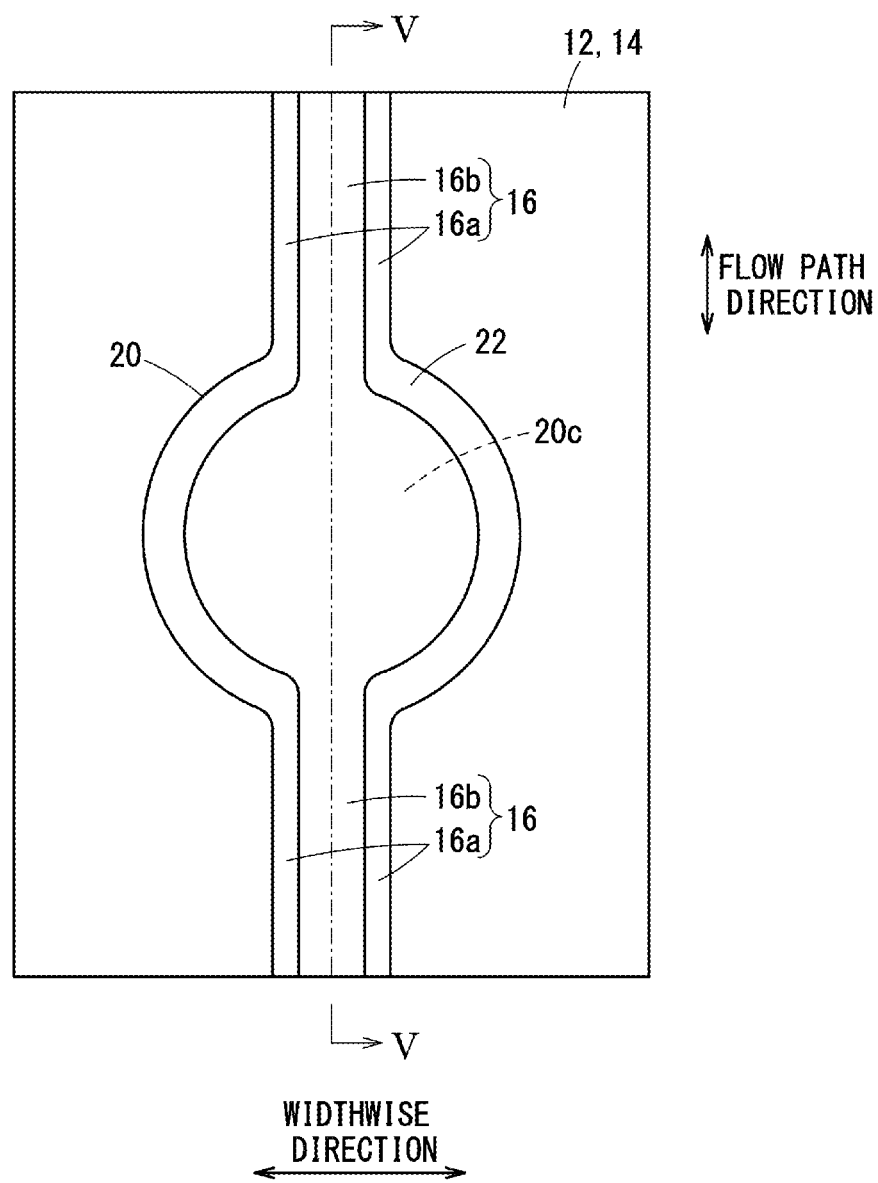
FIG. 4 is a plan view of a structure formed in the step of FIG. 3 according to embodiments of the present disclosure.

Next, high frequency electrical power is supplied between the upper mold 28 and the lower mold 26 to thereby perform the first fusion bonding step. The portions of the resin sheets 12 and 14 that are pressed from above and below by the pressing parts 26a of the lower mold 26 and the pressing parts 28a of the upper mold 28 are heated and fusion bonded together by the high frequency electrical power. Consequently, as shown in FIG. 4, the flow paths 16, and the widened portion 20 where the pair of resin sheets 12 and 14 are fusion bonded together are formed. Further, the resin sheets 12 and 14 at the flow paths 16, and the widened portion 20 are shaped in a bulging shape by being fusion bonded while pressurized air is supplied thereto.

Figure 5:
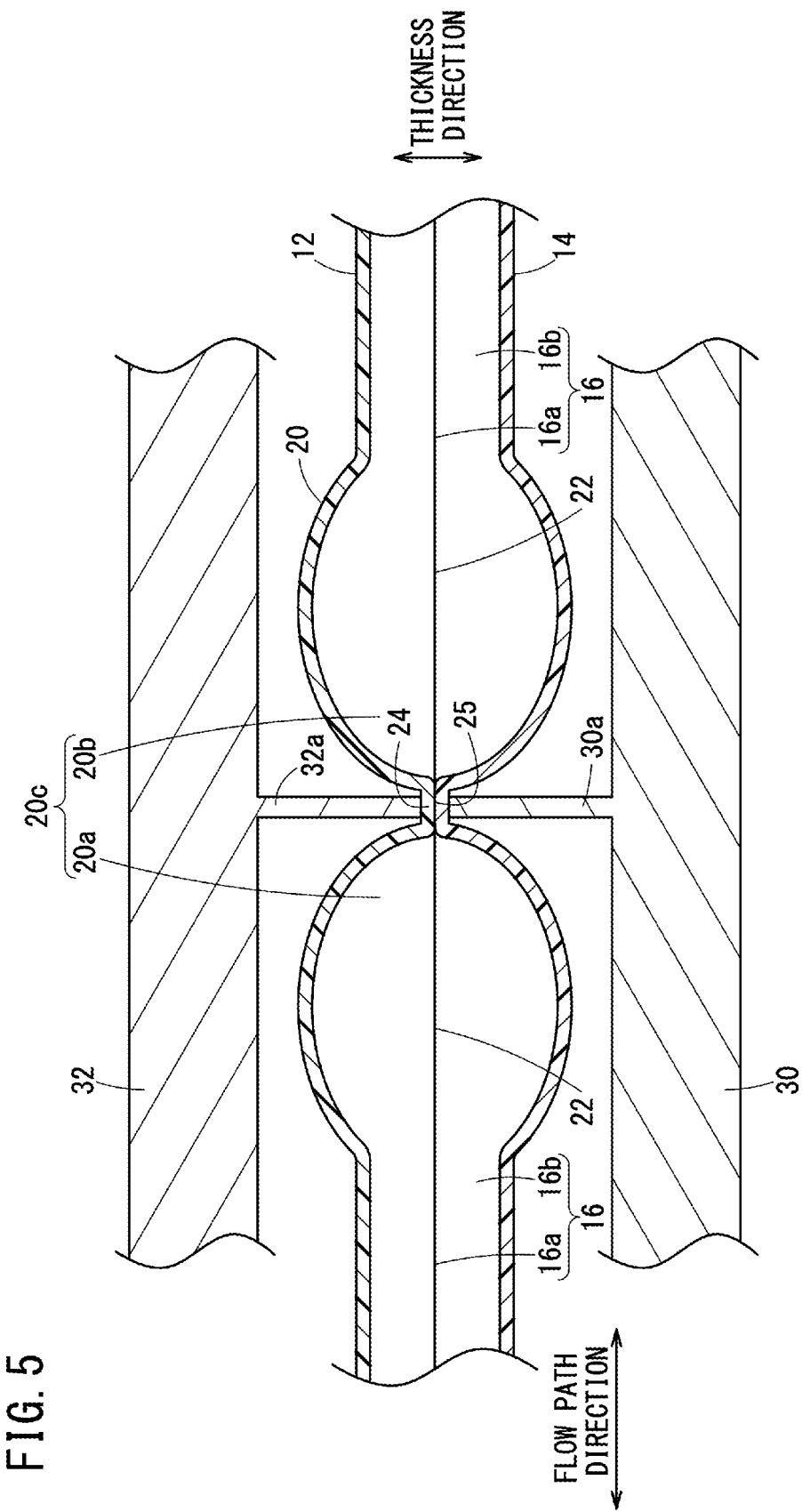
FIG. 5 is a cross-sectional view taken along line V-V of FIG. 4 and showing a second fusion bonding step in the method of manufacturing the flow path sealing structure shown in FIG. 1A according to embodiments of the present disclosure.

Next, the second fusion bonding step is performed. As shown in FIG. 5, the second fusion bonding step is carried out using a lower mold 30 having a pressing part 30a at a portion corresponding to the weakly sealed portion 24, and an upper mold 32 having a pressing part 32a at a portion facing toward the pressing part 30a. The structure shown in FIG. 4 is arranged between the lower mold 30 and the upper mold 32. Thereafter, portions of the resin sheets 12 and 14 corresponding to the weakly sealed portion 24 are sandwiched between the pressing parts 30a and 32a. Then, high frequency electrical power is supplied between the lower mold 30 and the upper mold 32 to thereby fusion bond the resin sheets 12 and 14 that are sandwiched between the pressing parts 30a and 32a.

By adjusting the electrical power supplied to the lower mold 30 and the upper mold 32, the second fusion bonding step is carried out under a condition in which the amount of input heat per unit area of the fusion bonded portion is less than in the first fusion bonding step. Consequently, the resin sheets 12 and 14 are fusion bonded in a state in which the interface 25 (see FIG. 2B) is left remaining therebetween, and the weakly sealed portion 24 having an appropriate sealing strength is formed. In the manner described above, manufacturing of the flow path sealing structure 10 according to embodiments of the present disclosure is completed.

Hereinafter, a description will be given concerning the result of producing the flow path sealing structure 10 having various dimensions, and examining a relationship between heating conditions in the second fusion bonding step and the sealing strength. In this instance, the diameter (width) of the widened portion 20 is variously changed, and an evaluation of the sealing strength of the weakly sealed portion 24 is performed when the electrical power (e.g., input heat) supplied in the second fusion bonding step is changed within a range of 20 to 70 W. The sealing strength of the weakly sealed portion 24 was evaluated by determining a pressure (e.g., opening pressure) when the weakly sealed portion 24 breaks upon supplying fluid from the one flow path 16. An appropriate opening pressure for the flow path sealing structure 10 according to embodiments of the present disclosure was evaluated as being appropriate when the lower limit thereof was within a range on the order of 0.1 MPa and an upper limit thereof was within a range on the order of 0.2 MPa. When the opening pressure is less than a value in proximity to 0.1 MPa, since the sealing strength starts to become insufficient, a concern arises in that opening may easily occur in the case that an unintended load acts thereon during handling. Further, when the opening pressure exceeds a value in proximity to 0.2 MPa, it becomes difficult for opening to occur even if a pressure is applied thereto by the operator, and ease of handling tends to deteriorate.

In Exemplary Embodiment 1, the diameter (e.g., width) of the widened portion 20 was set to 15.5 mm. In Exemplary Embodiment 2, the diameter (e.g., width) of the widened portion 20 was set to 13.5 mm. Further, in Exemplary Embodiment 3, the diameter (e.g., width) of the widened portion 20 was set to 13.5 mm. Further, in Exemplary Embodiment 4, the diameter (e.g., width) of the widened portion 20 was set to 9.5 mm. On the other hand, in the Comparative Example, without providing the widened portion 20, only the weakly sealed portion 24 was provided in the flow path 16. Moreover, in Exemplary Embodiments 1 to 4 and the Comparative Example, the width of the flow paths 16 was 2.8 mm, and the average dimension of the weakly sealed portion 24 in the flow path direction was 3 mm.

Figure 6:
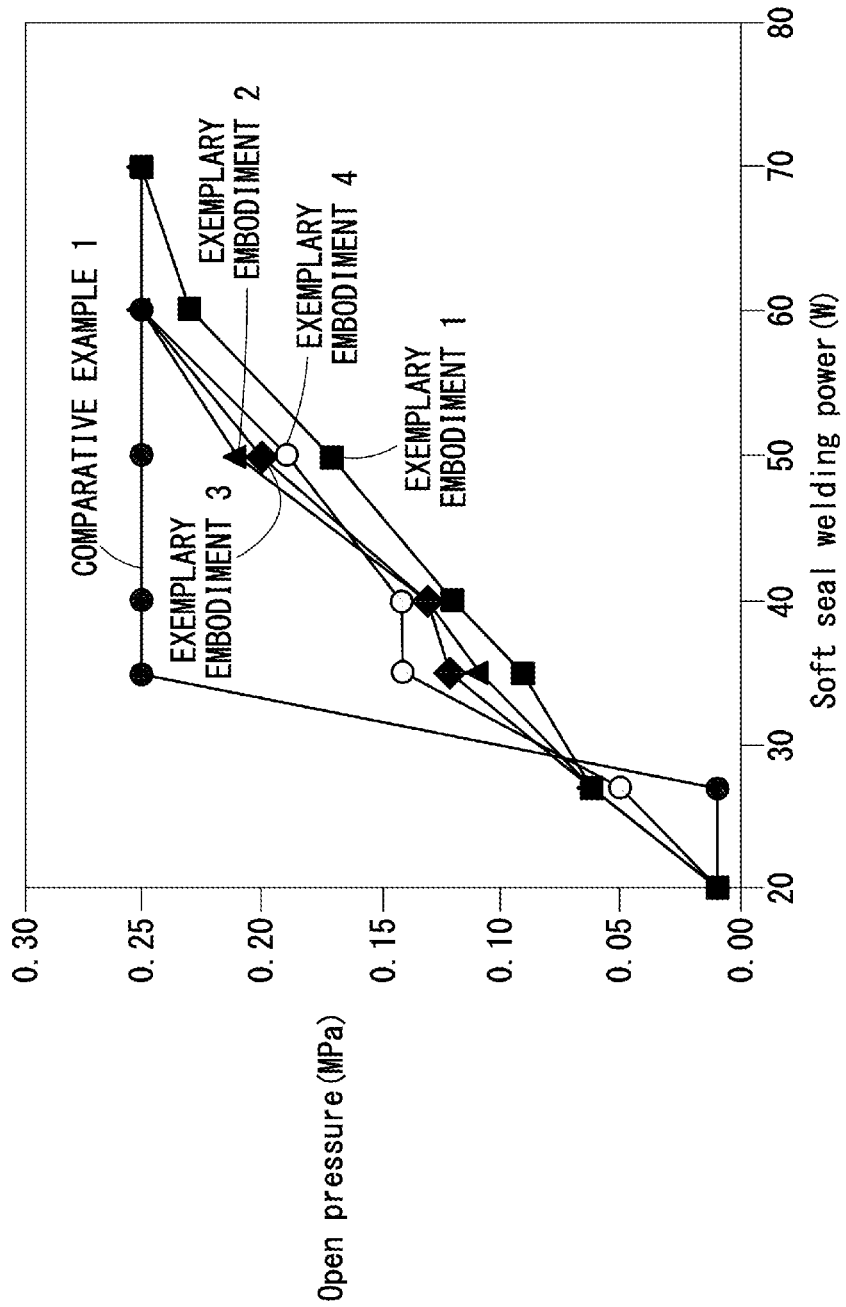
FIG. 6 is a graph showing the results of measuring a relationship between a sealing power and a sealing strength in the second fusion bonding step, in flow path sealing structures according to embodiments of the present disclosure.

The results of Exemplary Embodiments 1 to 4 and the Comparative Example are shown in FIG. 6. As shown in the graph, in the case that the widened portion 20 is provided, it was understood that the sealing strength of the weakly sealed portion 24 gradually changes accompanying an increase in the electrical power supplied in the second fusion bonding step. Accordingly, in Exemplary Embodiments 1 to 4, due to the electrical power supplied in the second fusion bonding step, it was possible to confirm that the weakly sealed portions 24 of various sealing strengths can be formed, and the weakly sealed portion 24 having a desired sealing strength can be manufactured.

In the foregoing manner, by providing the widened portion 20 in the flow path sealing structure 10, manufacturing of the weakly sealed portion 24 of a desired sealing strength is made possible.

Moreover, by locally modifying the materials or their mixing ratio of the resin sheets 12 and 14 on the inner side of the widened portion 20 that is capable of constituting the weakly sealed portion 24 so as to be made different from the materials or their mixing ratio of other portions, the weakly sealed portion 24 may be controlled in a manner so that the sealing strength of the weakly sealed portion 24 becomes weaker than the sealing strength of the other portions. In this case, there is no need to perform fusion bonding twice with differing amounts of input heat, and the weakly sealed portion 24 can be formed by a single fusion bonding step.

The flow path sealing structure 10 according to embodiments of the present disclosure exhibits the following advantageous effects.

The flow path sealing structure 10 according to embodiments of the present disclosure is characterized by the flow path sealing structure 10, which is disposed on the way of the flow path 16 formed by fusion bonding the pair of resin sheets 12 and 14 that are superimposed on each other, and includes the widened portion 20 surrounded by the widened seal portion 22 formed by fusion bonding the pair of resin sheets 12 and 14 around the periphery thereof, and the one end and the other end of which are in communication with the flow path 16, the widened portion 20 being formed to be wider than the flow path 16, and the weakly sealed portion 24 formed to extend in the widthwise direction in the widened portion 20, and which partitions the widened portion 20 in a liquid-tight and airtight manner into the first region 20a on the side of the one end and the second region 20b on the side of the other end, the weakly sealed portion 24 configured to be opened by increasing the internal pressure of the widened portion 20.

In accordance with the above-described constitution, the ability to control the sealing strength of the weakly sealed portion 24 can be improved, and it is possible to form the weakly sealed portion 24 with an appropriate sealing strength. Consequently, the flow path sealing structure 10, which is capable of reliably sealing the flow paths 16 and can be easily opened when necessary, can be integrally manufactured in the resin sheets 12 and 14 together with the flow paths 16.

In the above-described flow path sealing structure 10, the weakly sealed portion 24 may be fusion bonded in a state in which the interface 25 is left remaining between the pair of resin sheets 12 and 14. In accordance with this feature, the flow path sealing structure 10 can be easily opened.

In the above-described flow path sealing structure 10, the dimension of the weakly sealed portion 24 in a direction (e.g., the flow path direction) perpendicular to the widthwise direction may be formed in a curving manner so as to become smaller toward the center in the widthwise direction. In accordance with such constitution, the resin sheets 12 and 14 adjacent to the weakly sealed portion 24 are likely to bulge in a manner so as to separate away from each other due to the pressure of the fluid, and the ability to control the sealing strength is further improved.

In the above-described flow path sealing structure 10, the widened portion 20 may be formed in a circular shape as viewed in plan. In accordance with such constitution, the resin sheets 12 and 14 adjacent to the weakly sealed portion 24 become likely to bulge, and control of the sealing strength is facilitated.

In the above-described flow path sealing structure 10, at the widened portion 20, the pair of resin sheets 12 and 14 may bulge in a manner so as to separate away from each other in the thickness direction. In accordance with such constitution, because the resin sheets 12 and 14 are likely to bulge when a pressure is applied thereto, control of the sealing strength is facilitated.

In the above-described flow path sealing structure 10, the first region 20a and the second region 20b need not necessarily be made to bulge. In accordance with such constitution, if there is a bulge, stresses will continue to be applied to the weakly sealed portion 24, and there is a possibility that pealing apart may take place. By making the first region 20a and the second region 20b flat, application of stress to the sealed portion can be eliminated.

The method of manufacturing a flow path sealing structure 10 according to embodiments of the present disclosure includes the step of superimposing the pair of resin sheets 12 and 14 in the thickness direction, the first fusion bonding step of fusion bonding the pair of resin sheets 12 and 14 to thereby form the flow path 16, and the widened portion 20 disposed on the way of the flow path 16 and which is formed to be wider than the flow path 16, and the second fusion bonding step of fusion bonding the resin sheets 12 and 14 of the widened portion 20 to thereby form the weakly sealed portion 24 that crosses in the widthwise direction, wherein, in the second fusion bonding step, fusion bonding is carried out under a condition in which the amount of input heat per unit area is less than in the first fusion bonding step.

In the above-described method of manufacturing the flow path sealing structure 10, since the method can be realized simply by adding the second fusion bonding step of forming the weakly sealed portion 24 to the first fusion bonding step of forming the flow paths 16, the flow path sealing structure 10 can be formed with a fewer number of process steps than in a conventional flow path sealing structure in which the assembly of separate members is required. Further, by providing the weakly sealed portion 24 in the widened portion 20, the weakly sealed portion 24 can be formed with an appropriate sealing strength.

In the above-described method of manufacturing the flow path sealing structure 10, in the weakly sealed portion 24, the resin sheets 12 and 14 may be in close contact with the interface 25 left remaining therebetween. In accordance with this feature, the flow path sealing structure 10 which is capable of being reliably opened when needed is obtained.

In the above-described method of manufacturing the flow path sealing structure 10, the constituent materials of the resin sheets 12 and 14 that constitute the weakly sealed portion 24 may be controlled. In this case, the weakly sealed portion 24 may be formed at the same time as the first fusion bonding step, and with the same amount of heat input per area as other seal portions. Further, in this case as well, in the second fusion bonding step, the weakly sealed portion 24 may be formed with a smaller amount of input heat.

Figure 7:
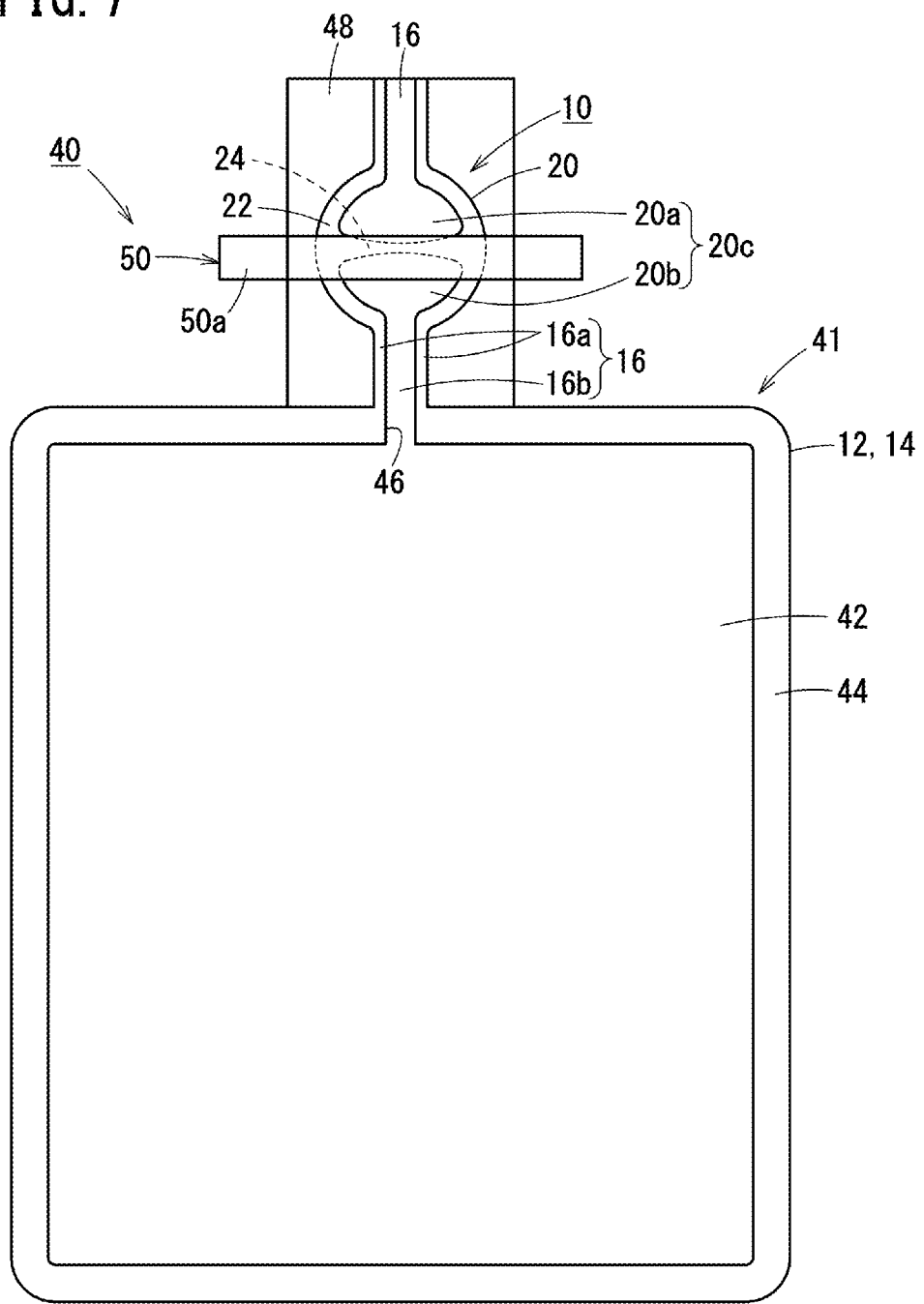
FIG. 7 is a plan view of a bag-shaped container according to embodiments of the present disclosure.

As shown in FIG. 7, the bag-shaped container 40 according to embodiments of the present disclosure includes a main body portion 41, the flow paths 16 that communicate with the main body portion 41, and the flow path sealing structure 10 disposed on the way of the flow paths 16. The bag-shaped container 40, for example, is a container for medical use in which a medicinal solution or the like is stored therein, and the flow paths 16 are used for introducing a liquid into the bag-shaped container 40, or for discharging the liquid from the bag-shaped container 40. In the bag-shaped container 40, the main body portion 41, the flow paths 16, and the flow path sealing structure 10 are integrally formed by the pair of resin sheets 12 and 14. Moreover, concerning structural features that are the same as those of the flow paths 16 and the flow path sealing structure 10 shown in FIG. 1A, they are designated by the same reference numerals, and detailed description of such features is omitted.

The main body portion 41 is formed in a substantially rectangular shape, and includes a peripheral edge sealed portion 44 formed by fusion bonding a peripheral edge part thereof, and an accommodating section 42 formed on an inner side of the peripheral edge sealed portion 44. The peripheral edge sealed portion 44 is constituted by a strong seal in which the resin sheets 12 and 14 are completely fusion bonded. The peripheral edge sealed portion 44 closes the peripheral edge part of the main body portion 41, together with being divided at a communicating section 46.

The accommodating section 42 is formed between the pair of resin sheets 12 and 14, and in the portion that is sealed by the peripheral edge sealed portion 44. The accommodating section 42 communicates with the flow paths 16 at the communicating section 46. Liquid contents are accommodated in the accommodating section 42.

A flow path formation unit 48 projects from one end of the main body portion 41. The flow path formation unit 48 is a portion in which the flow paths 16 and the flow path sealing structure 10 are formed, and is constituted by the resin sheets 12 and 14 which are integrally connected to the main body portion 41. The flow paths 16 communicate with the accommodating section 42, and the flow paths 16 are sealed by the flow path sealing structure 10. The flow path sealed portions 16a on both sides of the flow paths 16 are connected to the peripheral edge sealed portion 44 on both sides of the communicating section 46. In the flow path sealing structure 10, when the main body portion 41 is pressed, the weakly sealed portion 24 breaks and opens.

In the bag-shaped container 40 according to embodiments of the present disclosure, in order to prevent the weakly sealed portion 24 of the flow path sealing structure 10 from being inadvertently broken due to an increase in the internal pressure of the accommodating portion 42 when autoclave sterilization is performed or when subjected to handling or the like, an opening prevention member 50 is attached to the flow path formation unit 48. The opening prevention member 50 is disposed at a position overlapping the weakly sealed portion 24 of the flow path sealing structure 10, and by being placed in abutment from both sides in the thickness direction of the weakly sealed portion 24, the resin sheets 12 and 14 at a location in close proximity to the weakly sealed portion 24 are prevented from rising upward, and breakage of the weakly sealed portion 24 is prevented. The opening prevention member 50 is a clamp equipped with a pair of rod-shaped holding members 50a, and holds the resin sheets 12 and 14 by an elastic biasing force of the holding members 50a. In use, the opening prevention member 50 can be easily removed by pulling off the holding members 50a from the resin sheets 12 and 14. Moreover, it should be noted that the opening prevention member 50 is not limited to such an illustrated clamp, and may be constituted so as to press the weakly sealed portion 24 by being formed integrally with a packaging body in which the bag-shaped container 40 is accommodated.

Hereinafter, a description will be given concerning a method of manufacturing the bag-shaped container 40 according to embodiments of the present disclosure.

Figure 8:
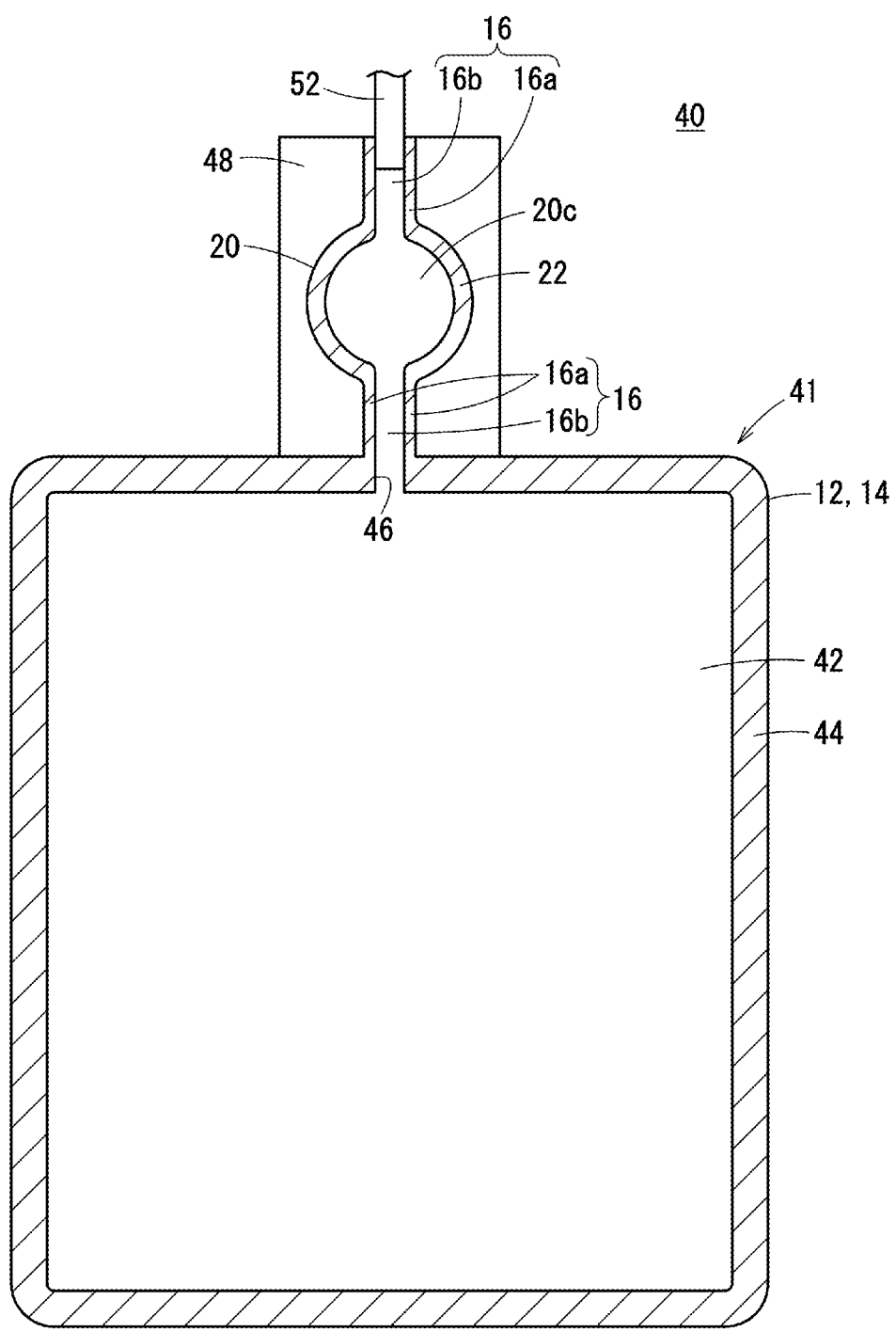
FIG. 8 is an explanatory diagram showing a first fusion bonding step of the bag-shaped container shown in FIG. 7 according to embodiments of the present disclosure.

First, the pair of resin sheets 12 and 14 are prepared, and the resin sheets 12 and 14 are superimposed on each other in the thickness direction. Next, the superimposed resin sheets 12 and 14 are sandwiched between a lower mold and an upper mold of a predetermined shape, and the portion shown in hatching in FIG. 8 is pressed. In addition, a first fusion bonding step is carried out in which high frequency electrical power is supplied between the lower mold and the upper mold to thereby fusion bond the portion shown in hatching, and thereby form the peripheral edge sealed portion 44, the flow path sealed portions 16a, and the widened seal portion 22.

The first fusion bonding step is performed under a condition in which fusion takes place until the interface 25 between the resin sheets 12 and 14 disappears. Further, in the first fusion bonding step, as shown in the drawing, a nozzle 52 is inserted between the resin sheets 12 and 14, and by supplying high pressure air from the nozzle 52, fusion bonding is carried out while the portions surrounded by the peripheral edge sealed portion 44, the flow path sealed portions 16a, and the widened seal portion 22 are made to undergo bulging. The nozzle 52 is pulled out after fusion bonding of the other peripheral edge part is completed, and the portion where the nozzle 52 is inserted is fusion bonded to complete the first fusion bonding step.

Thereafter, a trimming step of cutting off an excess portion of the resin sheets 12 and 14 is performed. The trimming step is performed by placing the structure shown in FIG. 8 inside a mold provided with a cutting blade, and cutting and removing the excess portion. Moreover, instead of the trimming step, cutting blades for cutting off the excess portion of the resin sheets 12 and 14 may be provided on the lower mold and the upper mold that were used in the first fusion bonding step, and simultaneously with the resin sheets 12 and 14 being pressed by the lower mold and the upper mold, the main body portion 41 and the flow path formation unit 48 may be formed into predetermined shapes.

Thereafter, as necessary, a medicinal solution injection step of injecting a medicinal solution into the accommodating section 42 via the flow paths 16 is performed. In the case that the bag-shaped container 40 is manufactured in the form of an empty bag, the medicinal solution injection step is not performed.

Figure 9:
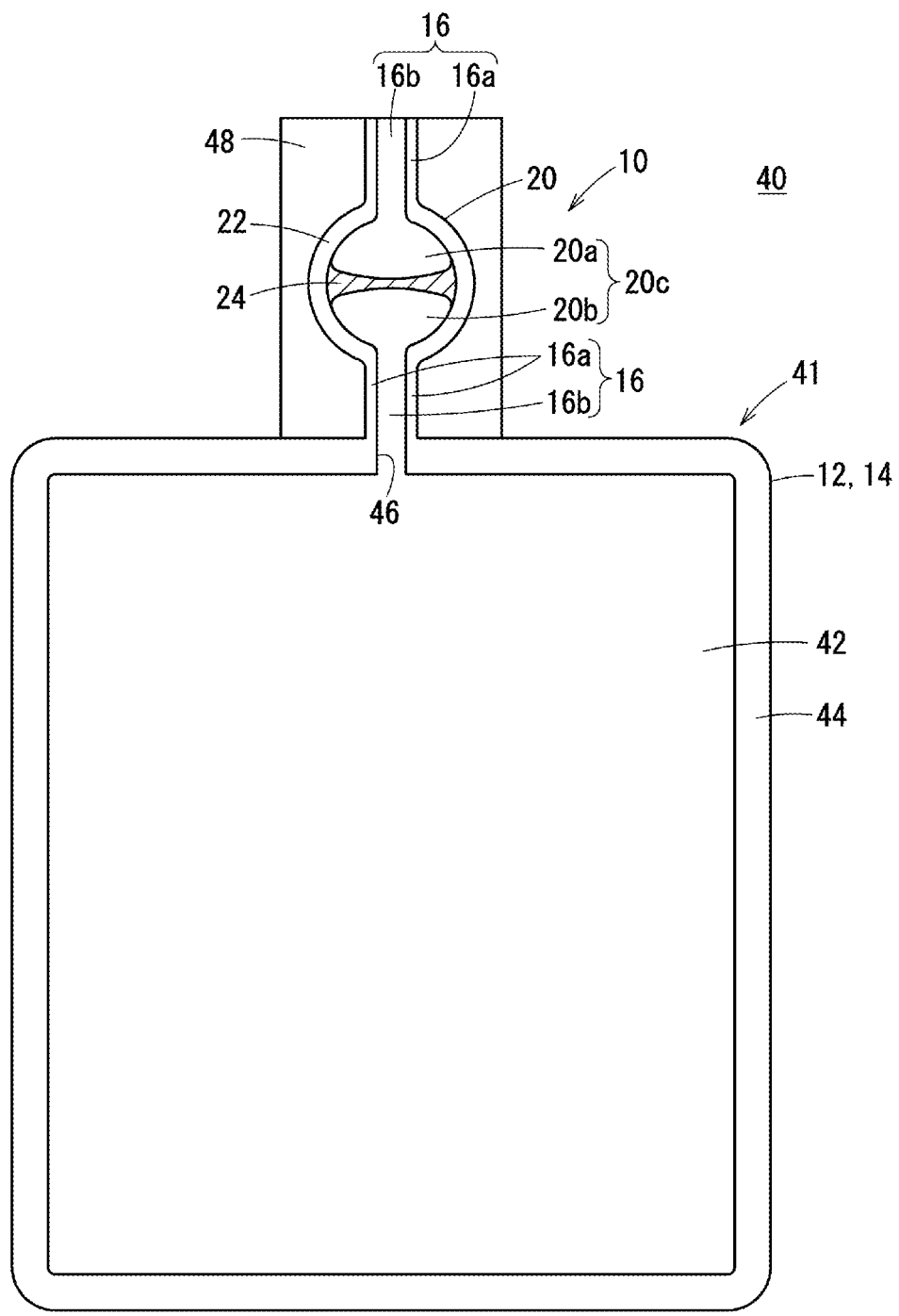
FIG. 9 is an explanatory diagram showing a second fusion bonding step of the bag-shaped container shown in FIG. 7 according to embodiments of the present disclosure.

Next, as shown in FIG. 9, a second fusion bonding step is performed in order to form the weakly sealed portion 24 in the widened portion 20. The second fusion bonding step can be performed by the same method that was described with reference to FIG. 5. Consequently, as shown in FIG. 9, the weakly sealed portion 24 is formed, and the flow path sealing structure 10 is completed. The accommodating section 42 is sealed by the flow path sealing structure 10. In accordance with the above procedure, the basic constitution of the bag-shaped container 40 is completed.

Thereafter, as shown in FIG. 7, an opening prevention member 50 is attached to a portion that overlaps the weakly sealed portion 24. In addition, the bag-shaped container 40 to which the opening prevention member 50 has been attached is inserted into an autoclave device, and autoclave sterilization is carried out. During autoclave sterilization, the internal pressure of the accommodating section 42 of the bag-shaped container 40 rises, however, the opening prevention member 50 prevents opening of the flow path sealing structure 10. In accordance with the above procedure, the method of manufacturing the bag-shaped container 40 according to embodiments of the present disclosure is brought to an end.

The bag-shaped container 40 according to embodiments of the present disclosure exhibits the following advantageous effects.

The bag-shaped container 40 according to embodiments of the present disclosure is characterized by the bag-shaped container 40 including the peripheral edge sealed portion 44 obtained by fusion bonding the pair of resin sheets 12 and 14 that are superimposed on each other, the accommodating section 42 surrounded by the peripheral edge sealed portion 44, the flow path 16 formed by fusion bonding the pair of resin sheets 12 and 14 and which are placed in communication with the accommodating section 42, and the flow path sealing structure 10 disposed on the way of the flow path 16, the flow path sealing structure 10 including the widened portion 20 surrounded by the widened seal portion 22 formed by fusion bonding the pair of resin sheets 12 and 14 around the periphery thereof, and the one end and the other end of which are in communication with the flow path 16, the widened portion 20 being formed to be wider than the flow path 16, and the weakly sealed portion 24 formed to extend in the widthwise direction in the widened portion 20, and which partitions the widened portion 20 in a liquid-tight and airtight manner into the first region 20a on the side of the one end and the second region 20b on the side of the other end, the weakly sealed portion 24 configured to be opened by increasing the internal pressure of the widened portion 20.

In accordance with the above-described constitution, since the flow paths 16 and the flow path sealing structure 10 are formed integrally with the bag-shaped container 40, production efficiency is superior. Further, by being equipped with the flow path sealing structure 10 in which the weakly sealed portion 24 is provided in the widened portion 20, the ability to control the sealing strength is excellent.

In the above-described bag-shaped container 40, the weakly sealed portion 24 may be fusion bonded in a state in which the interface 25 (see, e.g., FIG. 2B) is left remaining between the pair of resin sheets 12 and 14. In accordance with this feature, the flow path sealing structure 10 can be easily opened by pressing the bag-shaped container 40.

In the above-described bag-shaped container 40, the dimension of the weakly sealed portion 24 in a direction perpendicular to the widthwise direction may be formed in a curving manner so as to become smaller toward the center in the widthwise direction. Further, in the bag-shaped container 40, the widened portion 20 may be formed in a circular shape as viewed in plan. Further, in the bag-shaped container 40, at the widened portion 20, the pair of resin sheets 12 and 14 may bulge so as to separate away from each other in the thickness direction. In accordance with the above-described constitution, the resin sheets 12 and 14 at a location in close proximity to the weakly sealed portion 24 are likely to bulge, and the ability to control the sealing strength of the weakly sealed portion 24 is improved.

In the above-described bag-shaped container 40, there may further be provided the opening prevention member 50 that prevents the weakly sealed portion 24 from separating in the thickness direction. In accordance with this feature, even in the case that the internal pressure of the accommodating section 42 increases during autoclave sterilization, opening of the flow path sealing structure 10 can be prevented.

The method of manufacturing the bag-shaped container 40 according to embodiments of the present disclosure includes the step of superimposing the pair of resin sheets 12 and 14 in the thickness direction, the first fusion bonding step of fusion bonding the pair of resin sheets 12 and 14 to thereby form the accommodating section 42, the flow path 16, and the widened portion 20 disposed on the way of the flow path 16 and which is formed to be wider than the flow path 16, and the second fusion bonding step of fusion bonding the resin sheets 12 and 14 of the widened portion 20 to thereby form the weakly sealed portion 24 that crosses in the widthwise direction, wherein, in the second fusion bonding step, fusion bonding is carried out under a condition in which the amount of input heat per unit area is less than in the first fusion bonding step. In accordance with the above-described manufacturing method, since the method can be realized simply by adding the second fusion bonding step of forming the weakly sealed portion 24 to the first fusion bonding step of forming the accommodating section 42, the flow paths 16, and the widened portion 20, the flow path sealing structure 10 can be added to the bag-shaped container 40 with a fewer number of process steps than in a conventional flow path sealing structure in which the assembly of separate members is required. Further, by providing the weakly sealed portion 24 in the widened portion 20, the weakly sealed portion 24 can be formed with an appropriate sealing strength.

In the above-described method of manufacturing the bag-shaped container 40, in the weakly sealed portion 24, the resin sheets 12 and 14 may be fusion bonded with the interface 25 (see, e.g., FIG. 2B) left remaining therebetween. In accordance with this feature, the flow path sealing structure 10 which is capable of being reliably opened when needed is obtained.

In the above-described method of manufacturing the bag-shaped container 40, there may further be included the step of heat sterilizing (e.g., autoclave sterilizing) the accommodating section 42, the flow path 16, and the widened portion 20 after the second fusion bonding step, and the heat sterilization step may be performed by attaching to the weakly sealed portion 24 the opening prevention member 50 that prevents the weakly sealed portion 24 from separating in the thickness direction. In accordance with this feature, even if the internal pressure of the accommodating section 42 rises during heat sterilization, breakage of the weakly sealed portion 24 can be prevented.

In accordance with the above-described method of manufacturing the bag-shaped container 40, the flow paths 16 and the flow path sealing structure 10 can be formed together with the bag-shaped container 40, simply by adding the second fusion bonding step of forming the weakly sealed portion 24 to the first fusion bonding step of forming the peripheral edge sealed portion 44 of the bag-shaped container 40. Consequently, the flow path sealing structure 10 can be formed in the bag-shaped container 40 with a fewer number of process steps than in a conventional flow path sealing structure in which the assembly of separate members is required. Further, by providing the weakly sealed portion 24 in the widened portion 20, the weakly sealed portion 24 can be formed with an appropriate sealing strength.

Figure 10A:
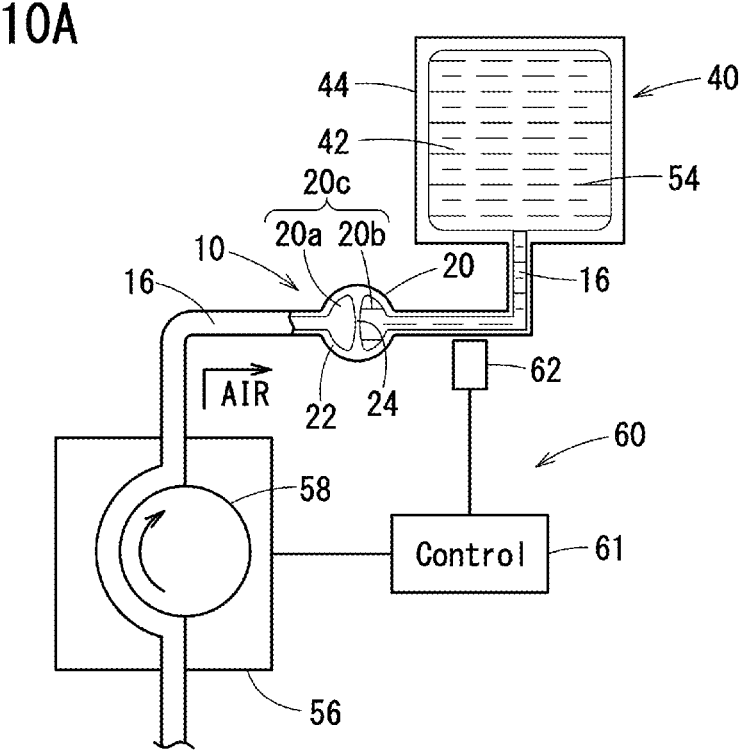
FIG. 10A is an explanatory diagram showing a transfer device according to embodiments of the present disclosure and an opening method of the flow path sealing structure according to embodiments of the present disclosure.

According to embodiments of the present disclosure, a description will be given concerning a method of opening the flow path sealing structure 10 shown in FIG. 7, as well as a transfer method of transferring fluid from the bag-shaped container 40. Moreover, in the following description, concerning constituent features that are the same as those of the bag-shaped container 40 shown in FIG. 7, they are designated by the same reference numerals, and detailed description of such features is omitted. The method according to embodiments of the present disclosure is performed using a transfer device 60 as shown in FIG. 10A. The transfer device 60, for example, is a device that constitutes a part of a blood sampling device or a centrifugal separation device, and by opening the flow path sealing structure 10 of the bag-shaped container 40 which has been set therein, is capable of transferring the fluid accommodated in the accommodating section 42.

As shown in the drawing, the transfer device 60 includes a pump 56, a control unit 61, and a sensor 62. The pump 56, for example, is a peristaltic pump, and is equipped with a rotor 58. The flow path 16 that extends from the bag-shaped container 40 is installed on the rotor 58 of the pump 56. By undergoing peristaltic motion, the rotor 58 is capable of transferring the fluid inside the flow paths 16.

The sensor 62, for example, is an optical sensor, and detects a component of the fluid inside the flow paths 16. The sensor 62 may also be a pressure sensor that detects the internal pressure of the flow paths 16. The control unit 61 controls operation of the pump 56 based on the detection result of the sensor 62.

Transferring of the fluid from the bag-shaped container 40 by the transfer device 60 is performed in the following manner. First, the flow paths 16 of the bag-shaped container 40 are set in the pump 56, and the opening prevention member 50 (see FIG. 7), which is attached to the flow path sealing structure 10, is removed.

Next, under the control of the control unit 61, the pump 56 is operated to rotate the rotor 58 in the direction of the arrow. Consequently, a pressurized fluid (for example, air) is sent into the flow path sealing structure 10 via the flow paths 16. By a predetermined pressure being applied to the flow path sealing structure 10, the resin sheets 12 and 14 in close proximity to the weakly sealed portion 24 bulge in a manner so as to be peeled apart, and the weakly sealed portion 24 is broken. Consequently, the flow path sealing structure 10 is opened.

The sensor 62 detects a change in the fluid component, and based thereon, the control unit 61 detects the opening of the flow path sealing structure 10. When the opening of the flow path sealing structure 10 is detected, the control unit 61 reverses the direction in which the rotor 58 of the pump 56 rotates.

Figure 10B:
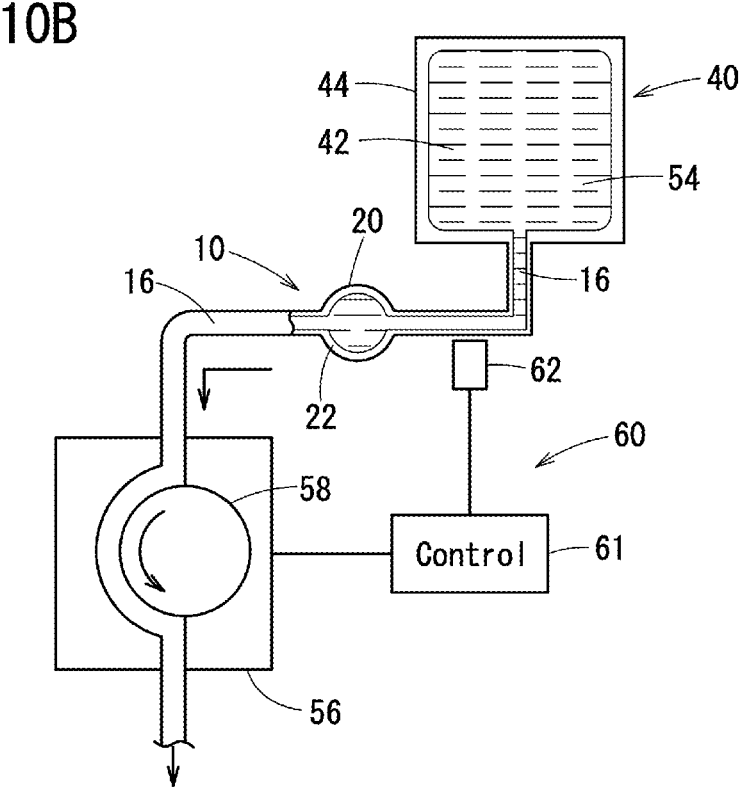
FIG. 10B is an explanatory diagram showing a fluid transferring method performed by the transfer device shown in FIG. 10A according to embodiments of the present disclosure.

As shown in FIG. 10B, by the rotor 58 rotating in the direction of the arrow, transferring of the fluid is started. The fluid contained in the bag-shaped container 40 is transferred by the pump 56 to the exterior through the flow paths 16. A predetermined amount of the fluid is transferred, whereupon transferring of the fluid is completed.

In the foregoing manner, according to the transfer device 60 according to embodiments of the present disclosure, it is possible for opening of the flow path sealing structure 10 and transferring of the fluid in the bag-shaped container 40 to be carried out.

The method of opening the flow path sealing structure 10 according to embodiments of the present disclosure and the transfer method of transferring the fluid exhibit the following advantageous effects.

In the method of opening the flow path sealing structure 10 according to embodiments of the present disclosure, the flow path sealing structure 10 is disposed on the way of the flow path 16 formed by fusion bonding the pair of resin sheets 12 and 14 that are superimposed on each other, and includes the widened portion 20 surrounded by the widened seal portion 22 formed by fusion bonding the pair of resin sheets 12 and 14 around the periphery thereof, and one end and another end of which are in communication with the flow path 16, the widened portion 20 being formed to be wider than the flow path 16, and the weakly sealed portion 24 formed to extend in the widthwise direction in the widened portion 20, and which partitions the widened portion 20 in a liquid-tight and airtight manner into the first region 20a on the side of the one end and the second region 20b on the side of the other end, the weakly sealed portion 24 configured to be opened by increasing the internal pressure of the widened portion 20, the method of opening the flow path sealing structure 10 including the step of connecting the pump 56 to the flow path 16, and the step of sending the pressurized fluid into the widened portion 20 through the pump 56, and causing the pair of resin sheets 12 and 14 that constitute the weakly sealed portion 24 to separate. According to such a method of opening, the fluid, which has been pressurized by the pump 56, is sent therein, whereby opening of the flow path sealing structure 10 can be performed without the need for human intervention.

The transfer method according to embodiments of the present disclosure is a transfer method applied to the bag-shaped container 40, the bag-shaped container 40 including the peripheral edge sealed portion 44 obtained by fusion bonding the pair of resin sheets 12 and 14 that are superimposed on each other, the accommodating section 42 surrounded by the peripheral edge sealed portion 44, the flow path 16 formed by fusion bonding the pair of resin sheets 12 and 14 and which are placed in communication with the accommodating section 42, and the flow path sealing structure 10 disposed on the way of the flow path 16, the flow path sealing structure 10 including the widened portion 20 surrounded by the widened seal portion 22 formed by fusion bonding the pair of resin sheets 12 and 14 around the periphery thereof, and the one end and the other end of which are in communication with the flow path 16, the widened portion 20 being formed to be wider than the flow path 16, and the weakly sealed portion 24 formed to extend in the widthwise direction in the widened portion 20, and which partitions the widened portion 20 in a liquid-tight and airtight manner into the first region 20a on the side of the one end and the second region 20b on the side of the other end, the weakly sealed portion 24 configured to be opened by increasing the internal pressure of the widened portion 20. Such a transfer method includes the step of connecting the pump 56 to the flow path 16, the step of sending the pressurized fluid toward the flow path sealing structure 10 and into the accommodating section 42 through the pump 56, and causing the pair of resin sheets 12 and 14 that constitute the weakly sealed portion 24 of the flow path sealing structure 10 to separate, and the step of reversing the pump 56 and causing the fluid in the accommodating section 42 to flow out from the accommodating section 42. In accordance with these features, opening of the flow path sealing structure 10 of the bag-shaped container 40, and transferring of the fluid in the accommodating portion 42 can be performed without the need for human intervention.

A description will be given concerning a blood bag system 70 according to embodiments of the present disclosure, which is used for collecting and separating blood for use in products or for use in blood transfusions. Moreover, concerning constituent features that are the same as those of the flow path sealing structure 10 shown in FIG. 1A, they are designated by the same reference numerals, and detailed description of such features is omitted.

Figure 11:
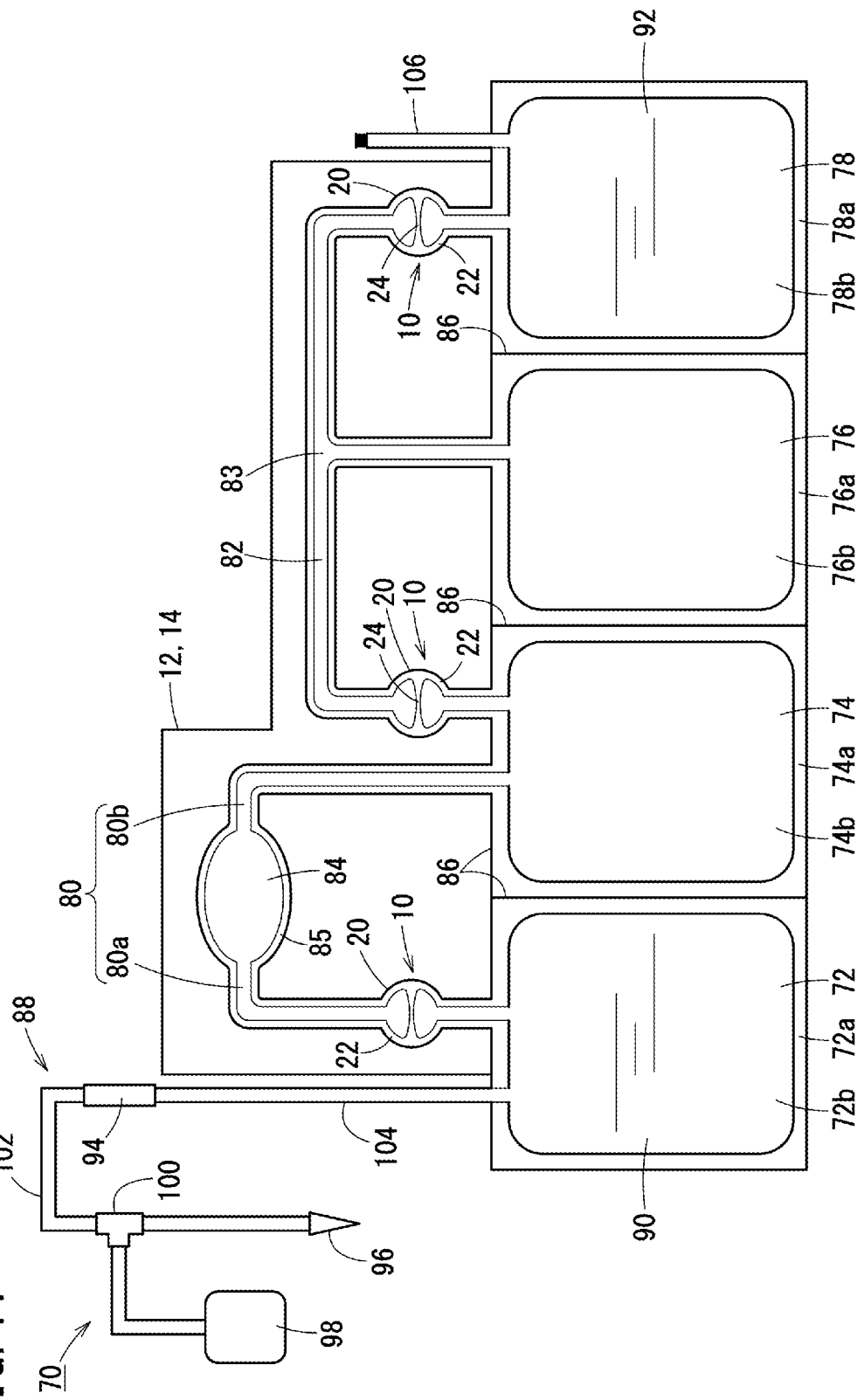
FIG. 11 is a plan view of a blood bag system according to embodiments of the present disclosure.

As shown in FIG. 11, the blood bag system 70 according to embodiments of the present disclosure serves as a system for centrifugally separating blood containing a plurality of components into a plurality of components having different specific gravities (for example, two components of a light specific gravity component and a heavy specific gravity component), and accommodating and storing the respective components in different bags. The blood bag system 70 according to embodiments of the present disclosure is constituted so as to centrifugally separate the remaining blood components, in which white blood cells and blood platelets have been removed from whole blood, into two components of blood plasma and concentrated red blood cells, and to accommodate and store the plasma and the concentrated red blood cells by dividing them into different bags.

The blood bag system 70 includes a blood collection unit 88 that collects blood from a donor, a blood collection bag 72 in which collected whole blood is accommodated, a preprocessing unit that removes predetermined blood components from the whole blood, a parent bag 74 and a child bag 76 in which remaining blood components from which predetermined components have been removed are centrifugally separated and divided into a plurality of blood components that are accommodated therein, and a medicinal solution bag 78 for supplying a red blood cell storage solution 92 to the parent bag 74.

The blood collection unit 88 is equipped with tubes 102 and 104, a branch connector 100, a breakable member 94, a blood collection needle 96, and an initial flow blood bag 98.

The branch connector 100 is equipped with first to third ports. The blood collection needle 96 is connected to the first port, the initial flow blood bag 98 is connected to the second port, and the third port is connected to the blood collection bag 72 via the breakable member 94 and the tube 104. The blood collection needle 96 has a needle tip that is punctured into the skin of the donor, and is a part into which blood from the donor flows when blood collection from the donor is carried out.

The initial flow of blood when blood is collected flows through the second port of the branch connector 100, and is accommodated in the initial flow blood bag 98. The initial flow blood bag 98 accommodates a predetermined amount of the initial flow of blood.

The tube 102 is connected to the third port of the branch connector 100, and the other end is connected to one end of the breakable member 94. The breakable member 94 is constituted in a manner so that the flow path is closed in an initial state, however, the flow path is opened by performing a breaking operation. The blood collection bag 72 is connected via the tube 104 to the other end of the breakable member 94. The breakable member 94 is subjected to the breaking operation after the initial flow of blood is collected in the initial flow blood bag 98. The whole blood collected from the donor flows into the blood collection bag 72 through the opened breakable member 94. The tube 104 is made from a thermoplastic resin or the like, and together with being fusion bonded and sealed by a tube sealer or the like, is constituted to be cut after the completion of blood collection.

The blood collection bag 72 is formed in a bag shape by superimposing the pair of resin sheets 12 and 14, and fusion bonding (e.g., heat fusion bonding or high frequency fusion bonding) a peripheral edge sealed portion 72a of the peripheral edge part. Further, it is preferable that the resin sheets 12 and 14 use transparent or translucent resin sheets 12 and 14, in order to facilitate optical discrimination between blood plasma and the concentrated red blood cells when the blood components are transferred through a later-described second flow path 82. The blood collection bag 72 preferably contains an anticoagulant 90 in order to prevent coagulation of the blood (e.g., whole blood). The anticoagulant 90 is normally a liquid, examples of which include an ACD-A solution, a CPD solution, a CPDA-1 solution, and a heparin sodium solution. The amount of the anticoagulant 90 is an appropriate amount in accordance with the expected amount of blood to be collected.

The tube 102 and a flow path 80a are connected to the blood collection bag 72. The flow path 80a communicates with an accommodating section 72b of the blood collection bag 72. The flow path sealing structure 10 is disposed on the way of the flow path 80a, and the flow path 80a is sealed by the flow path sealing structure 10 in an initial state.

The preprocessing unit includes a filter 84 for removing predetermined cells, an inlet-side flow path 80a, and an outlet-side flow path 80b. The inlet-side flow path 80a and the outlet-side flow path 80b constitute a first flow path 80 connecting the blood collection bag 72 and a parent bag 74. The inlet-side flow path 80a is a flow path for transferring blood collected from the donor from the blood collection bag 72 to the filter 84.

The outlet-side flow path 80b is a flow path for transferring the blood that has passed through the filter 84 to the parent bag 74. The outlet-side flow path 80b and the inlet-side flow path 80a are formed by fusion bonding the resin sheets 12 and 14, and are integrally connected to the blood collection bag 72.

The filter 84 removes predetermined cells when the blood is transferred from the blood collection bag 72 to the parent bag 74. According to embodiments of the present disclosure, the filter 84 is a leukocyte removing filter. In such a leukocyte removing filter, a filter medium made of a liquid-permeable porous body or a non-woven fabric can be used. The filter 84 may be constituted in a manner so as to also capture platelets. The filter 84 is disposed between the resin sheets 12 and 14, and is sealed on the inner side of a filter sealed portion 85 formed by being fusion bonded along a peripheral edge part thereof.

In the same manner as the blood collection bag 72, the parent bag 74, the child bag 76, and the medicinal solution bag 78 are formed by superimposing the pair of resin sheets 12 and 14, and are integrally connected to each other via the second flow path 82. The parent bag 74 serves both as a bag for accommodating the residual blood from which predetermined cells have been removed by the filter 84, and a bag for storing a sedimentation component (e.g., rich red blood cells) obtained by centrifugally separating blood. The parent bag 74 is provided with a peripheral edge sealed portion 74a where a peripheral edge part thereof is subjected to fusion bonding, and an accommodating section 74b is formed on the inner side thereof. The outlet-side flow path 80b and the second flow path 82 are connected to the upper end of the parent bag 74.

The second flow path 82 is a flow path that is formed by fusion bonding the resin sheets 12 and 14, and is formed by being integrally connected to the parent bag 74 and the like. The second flow path 82 is connected to the parent bag 74, together with being connected to the child bag 76 and the medicinal solution bag 78 via a branching member 83. In the second flow path 82, the flow path sealing structure 10 is provided respectively in the vicinity of the parent bag 74 and the medicinal solution bag 78.

The child bag 76 serves as a bag for storing a supernatant component (e.g., blood plasma) obtained by subjecting the parent bag 74 to centrifugation. The second flow path 82 is connected to the upper end of the child bag 76. The child bag 76 is connected to the parent bag 74 via the second flow path 82.

The medicinal solution bag 78 accommodates the red blood cell storage solution 92 that is supplied to the parent bag 74. As the red blood cell storage solution 92, there may be used a MAP solution, a SAGM solution, an OPTISOL solution, or the like. The second flow path 82 and the tube 106 are connected to the upper end of the medicinal solution bag 78. The tube 106 is a tube for injecting the medicinal solution into the medicinal solution bag 78, and is subjected to fusion bonding and sealed by a sealer or the like.

The blood collection bag 72, the parent bag 74, the child bag 76, and the medicinal solution bag 78 are separated from each other at cutting portions 86. The respective bags are integrally connected via the first flow path 80 and the second flow path 82.

Next, a description will be given in outline concerning a method of using the blood bag system 70.

In the blood bag system 70, blood (e.g., whole blood) is accommodated in the blood collection bag 72 through the blood collection unit 88. Thereafter, the user cuts and seals the tube 104 with a sealer, and separates the blood collection unit 88. Next, an opening operation is carried out on the flow path sealing structure 10, and the blood components of the blood collection bag 72 are transferred to the parent bag 74. At this time, leukocytes and blood platelets are removed by the filter 84 from the blood that is transferred from the blood collection bag 72. Thereafter, by cutting and fusion bonding the outlet-side flow path 80b with a sealer, the user separates the blood collection bag 72 and the filter 84 from the parent bag 74.

The parent bag 74, the child bag 76, and the medicinal solution bag 78 are set in the centrifugal separation device. In the centrifugal separation device, a centrifugal force is applied to the parent bag 74 to thereby separate the blood inside the parent bag 74 into a supernatant component of blood plasma and a sedimentation component of red blood cells, together with transferring the supernatant component of the blood platelets through the second flow path 82 into the child bag 76. The centrifugal separation device automatically opens the flow path sealing structure 10 provided in the second flow path 82, and transfers the supernatant component. Thereafter, a part of the second flow path 82 that extends toward the child bag 76 via the branching member 83 is closed by a clamp. In addition, the red blood cell storage solution 92 in the medicinal solution bag 78 is transferred to the parent bag 74 through the second flow path 82, whereupon the centrifugation process for the blood components is completed.

Hereinafter, a description will be given concerning a method of manufacturing the blood bag system 70 according to embodiments of the present disclosure.

First, the pair of resin sheets 12 and 14 which are formed in a predetermined shape are prepared, and the resin sheets 12 and 14 are superimposed on each other in the thickness direction. When the resin sheets 12 and 14 are superimposed, it is preferable that the filter 84, the tubes 104 and 106, and the like be positioned and temporarily fixed at predetermined positions beforehand.

Next, a first fusion bonding step is performed, and the resin sheets 12 and 14 are subjected to fusion bonding with a strong seal. More specifically, fusion bonding is carried out on the peripheral edge sealed portions 72a, 74a, 76a, and 78a, the fusion bonded portion of the first flow path 80, the fusion bonded portion of the second flow path 82, and the widened seal portion 22 (see, e.g., FIG. 1A) of the flow path sealing structure 10. In the first fusion bonding step, as shown in FIG. 3, the resin sheets 12 and 14 are sandwiched between the upper mold and the lower mold having a protruding portion at the fusion bonded portion, and while high pressure air is supplied to the region surrounded by the fusion bonded portion, fusion bonding is carried out by supplying high frequency electrical power to the lower mold and the upper mold.

Thereafter, a second fusion bonding step is carried out in order to form the weakly sealed portion 24 of the flow path sealing structure 10. The second fusion bonding step can be performed by the method described with reference to FIG. 5.

Thereafter, the anticoagulant 90 is injected into the blood collection bag 72 via the tube 104. After injection of the anticoagulant 90 is completed, the breakable member 94 and the blood collection unit 88 are attached to the tube 104. Further, the red blood cell storage solution 92 is injected into the medicinal solution bag 78 via the tube 106. After injection of the red blood cell storage solution 92 is completed, the tube 106 is cut and sealed with a sealer.

In accordance with the above procedure, the basic constitution of the blood bag system 70 is completed. Thereafter, autoclave sterilization is carried out on the blood bag system 70. When autoclave sterilization is carried out, it is preferable to attach an opening prevention member 50 (see, e.g., FIG. 7) in order to prevent opening of the flow path sealing structure 10. In accordance with the above procedure, manufacturing of the blood bag system 70 is completed.

Moreover, in the above-described blood bag system 70, the weakly sealed portion 24 can be opened by the operator squeezing the bag to thereby raise the internal pressure.

The blood bag system 70 according to embodiments of the present disclosure exhibits the following advantageous effects.

The blood bag system 70 according to embodiments of the present disclosure is characterized by the blood bag system 70 including the blood collection bag 72 in which whole blood is collected, the parent bag 74 in which centrifugal separation of the whole blood is carried out, the child bag 76 in which a portion of the separated blood component is accommodated, the medicinal solution bag 78 in which the red blood cell storage solution 92 for the blood component is accommodated, the first flow path 80 configured to connect the blood collection bag 72 and the parent bag 74, and the second flow path 82 configured to connect the parent bag 74, the child bag 76, and the medicinal solution bag 78, wherein the blood collection bag 72, the parent bag 74, the child bag 76, the medicinal solution bag 78, the first flow path 80, and the second flow path 82 are integrally formed by fusion bonding the pair of resin sheets 12 and 14, and there is provided the flow path sealing structure 10 disposed in at least one of the paths of the first flow path 80 and the second flow path 82, the flow path sealing structure 10 including the widened portion 20 surrounded by the widened seal portion 22 formed by fusion bonding the pair of resin sheets 12 and 14 around the periphery thereof, and the one end and the other end of which are in communication with the flow path 80 or 82, the widened seal portion 22 being formed to be wider than the flow path 80 or 82, and the weakly sealed portion 24 formed to extend in the widthwise direction in the widened portion 20, and which partitions the widened portion 20 in a liquid-tight and airtight manner into the first region 20a on the side of the one end and the second region 20b on the side of the other end, the weakly sealed portion 24 configured to be opened by increasing the internal pressure of the widened portion 20.

In accordance with the above-described blood bag system 70, since the flow path sealing structure 10 is formed integrally with the blood collection bag 72 and the like by the resin sheets 12 and 14, manufacturing costs can be suppressed.

According to embodiments of the present disclosure, as shown in FIG. 12A, a description will be given concerning an example in which the flow path sealing structure 10 is applied to a sample collecting structure 110 for a bag-shaped container 40A. Moreover, concerning constituent features that are the same as those of the flow path sealing structure 10 shown in FIG. 1A and the bag-shaped container 40 shown in FIG. 7, they are designated by the same reference numerals, and detailed description of such features is omitted.

The bag-shaped container 40A according to embodiments of the present disclosure is equipped with the main body portion 41 to which a connection port 107, and the sample collecting structure 110 are connected to an upper end thereof, and is constituted to be capable of sampling with the sample collecting structure 110 a portion of the liquid accommodated in the accommodating section 42 of the main body portion 41.

The bag-shaped container 40A is a container of a bag shape in which a pair of resin sheets 12 and 14 are superimposed on each other and fusion bonded at the peripheral edge sealed portion 44, and is capable of accommodating a liquid in the accommodating section 42 via the connection port 107 and a tube 108 that is connected to the connection port 107.

The sample collecting structure 110 includes a sample container 114 in which a collected liquid is accommodated, and flow paths 116 that connect the sample container 114 and the bag-shaped container 40A. The sample container 114, the flow paths 116, and the flow path sealing structure 10 that constitute the sample collecting structure 110 are formed by the pair of resin sheets 12 and 14 that constitute the bag-shaped container 40A. More specifically, the sample collecting structure 110 is integrally connected to the bag-shaped container 40A.

The flow paths 116 are equipped with flow path sealed portions 116a where the pair of resin sheets 12 and 14 are fusion bonded on both sides thereof, and flow through portions 116b are formed at portions surrounded by the flow path sealed portions 116a. One end of the flow paths 116 communicates with the accommodating section 42. Further, another end of the flow paths 116 communicates with the interior of the sample container 114. The flow path sealing structure 10 is disposed on the way of the flow paths 116, and one end and another end of the flow paths 116 are sealed by the flow path sealing structure 10.

The sample container 114 is provided with a peripheral edge sealed portion 114a which is formed by fusion bonding the resin sheets 12 and 14 at a peripheral edge part thereof, and an accommodating section 114b is formed on the inner side of the peripheral edge sealed portion 114a.

Hereinafter, a description will be given concerning a method of using the sample collecting structure 110 for the bag-shaped container 40A according to embodiments of the present disclosure. In the bag-shaped container 40A according to embodiments of the present disclosure, after a liquid which is a contained material has been injected into the accommodating section 42 of the main body portion 41, the tube 108 is sealed with a sealer and cut.

Thereafter, the accommodating section 42 is pressed to apply a pressure to the flow path sealing structure 10 through the flow paths 116, thereby opening the flow path sealing structure 10. In addition, the accommodating section 42 is further pressed to thereby transfer the liquid accommodated in the accommodating section 42 to the sample container 114. Thereafter, the flow path 116 is cut while being sealed with a sealer, and as shown in FIG. 12B, the sample collecting structure 110 is separated from the main body portion 41. The sample collecting structure 110 is used for testing or analysis.

The above described sample collecting structure 110 for the bag-shaped container 40A is manufactured by the following method.

The pair of resin sheets 12 and 14 which are formed in a predetermined shape are prepared, and after the connection port 107 has been temporarily fixed thereto at a predetermined position, the resin sheets 12 and 14 are superimposed on each other. Thereafter, the first fusion bonding step is performed to thereby form the peripheral edge sealed portions 44 and 114a, the flow path sealed portions 116a, and the widened seal portion 22. The first fusion bonding step is performed under a condition in which a strong seal is formed.

Thereafter, the second fusion bonding step is performed to thereby form the weakly sealed portion 24 in the flow path sealing structure 10. The second fusion bonding step can be performed by the same method that was described with reference to FIG. 5. Thereafter, the tube 108 is connected to the connection port 107 of the bag-shaped container 40A, whereupon the bag-shaped container 40A is completed. As necessary, the bag-shaped container 40A may be subjected to autoclave sterilization. In this case, it is preferable to attach the opening prevention member 50 (see FIG. 7) to the weakly sealed portion 24 of the flow path sealing structure 10.

Moreover, in the above-described blood bag system 70, the weakly sealed portion 24 can be opened by the operator squeezing the bag to thereby raise the internal pressure.

The sample collecting structure 110 for the bag-shaped container 40A according to embodiments of the present disclosure exhibits the following advantageous effects.

The sample collecting structure 110 for the bag-shaped container 40A includes the flow path 116 connected to the bag-shaped container 40A in which the accommodating section 42 is formed in the interior thereof, and which are placed in communication with the accommodating section 42, the sample container 114 connected to the bag-shaped container 40A via the flow path 116, and the flow path sealing structure 10 disposed on the way of the flow path 116 and configured to seal the flow path 116, wherein the flow path 116, the sample container 114, and the flow path sealing structure 110 are formed integrally with the bag-shaped container 40A by fusion bonding the pair of resin sheets 12 and 14. In addition, the flow path sealing structure 10 includes the widened portion 20 surrounded by the widened seal portion 22 formed by fusion bonding together the pair of resin sheets 12 and 14 around the periphery thereof, and the one end and the other end of which are in communication with the flow path 116, the widened seal portion 22 being formed to be wider than the flow path 116, and the weakly sealed portion 24 formed to extend in the widthwise direction in the widened portion 20, and which partitions the widened portion 20 in a liquid-tight and airtight manner into the first region 20a on the side of the one end and the second region 20b on the side of the other end, the weakly sealed portion 24 configured to be opened by increasing the internal pressure of the widened portion 20.

In the sample collecting structure 110 of the bag-shaped container 40A according to embodiments of the present disclosure, since the sample collecting structure 110 which includes the flow path sealing structure 10 can be simultaneously formed integrally with the pair of resin sheets 12 and 14 that constitute the bag-shaped container 40A, manufacturing costs can be suppressed.

Figure 13:
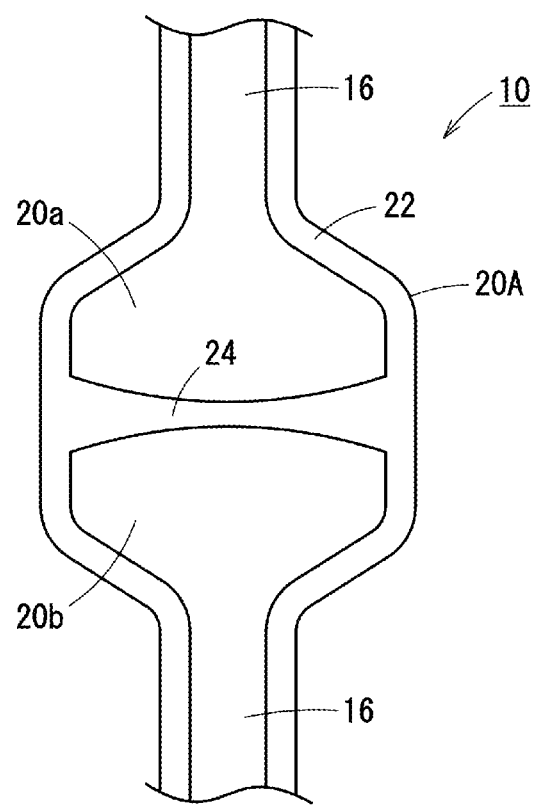
FIG. 13 is a plan view of a flow path sealing structure according to embodiments of the present disclosure.

In the above-described embodiments, an example of the widened portion 20 of the flow path sealing structure 10 was described as being formed in a circular shape as viewed in plan, however, the embodiments are not limited to this feature. For example, as shown in FIG. 13, a widened portion 20A that is formed in a rectangular shape as viewed in plan may also be provided. Such a widened portion 20A is formed in a rectangular shape in which the dimension thereof in the flow path direction extends longer than the dimension in the widthwise direction, and the weakly sealed portion 24 extends in the widthwise direction at a central part in the flow path direction. Even if the widened portion 20A according to embodiments of the present disclosure is applied to the flow path sealing structure 10, the same advantages and effects can be obtained.

Although preferred embodiments of the present disclosure have been described above, the present disclosure is not limited to the above-described embodiments, and it goes without saying that various modifications can be adopted therein without departing from the spirit and scope of the disclosure.

What is claimed is:

1. A flow path sealing structure disposed along a flow path formed by bonding a first resin sheet and a second resin sheet that are superimposed on each other, the flow path sealing structure comprising:

a widened portion surrounded by a widened seal portion formed by bonding the first resin sheet and the second resin sheet around a periphery of the widened portion, the widened portion including a first end and a second end both in communication with the flow path, wherein the widened portion is wider than the flow path; and a weakly sealed portion formed to extend in a widthwise direction in the widened portion, and that partitions the widened portion in a liquid-tight and airtight manner into a first region on the first end and a second region on the second end, the weakly sealed portion configured to be opened by increasing an internal pressure of the widened portion, wherein a material of the first and second resin sheets that forms the weakly sealed portion is different from a material of the first and second resin sheets that forms the widened seal portion.

2. The flow path sealing structure of claim 1, wherein the weakly sealed portion is bonded such that an interface remains between the first resin sheet and the second resin sheet.

3. The flow path sealing structure of claim 1, wherein a dimension of the weakly sealed portion in a direction perpendicular to the widthwise direction is formed in a curving manner so as to become smaller toward a center in the widthwise direction.

4. The flow path sealing structure of claim 1, wherein the widened portion is formed in a circular shape in a plan view.

5. The flow path sealing structure of claim 1, wherein, at the widened portion, the first and second resin sheets bulge so as to separate away from each other in a thickness direction.

6. A bag-shaped container comprising:
a peripheral edge sealed portion created by bonding a first resin sheet and a second resin sheet that are superimposed on each other;
an accommodating section surrounded by the peripheral edge sealed portion;
a flow path formed by bonding the first resin sheet and the second resin sheet, the flow path in communication with the accommodating section; and
a flow path sealing structure disposed along the flow path, the flow path sealing structure comprising:
a widened portion surrounded by a widened seal portion formed by bonding the first resin sheet and the second resin sheet around a periphery of the widening portion, the widening portion including a first end and a second end both in communication with the flow path, the widened portion wider than the flow path; and
a weakly sealed portion formed to extend in a widthwise direction in the widened portion, and that partitions the widened portion in a liquid-tight and airtight manner into a first region on the first end and a second region on the second end, the weakly sealed portion configured to be opened by increasing an internal pressure of the widened portion, wherein a material of the first and second resin sheets that forms the weakly sealed portion is different from a material of the first and second resin sheets that forms the widened seal portion.

7. The bag-shaped container of claim 6, wherein the weakly sealed portion is bonded such that an interface remains between the first and second resin sheets.

8. The bag-shaped container of claim 6, wherein a dimension of the weakly sealed portion in a direction perpendicular to the widthwise direction is formed in a curving manner so as to become smaller toward a center in the widthwise direction.

9. The bag-shaped container of claim 6, wherein the widened portion is formed in a circular shape in a plan view.

10. The bag-shaped container of claim 6, wherein, at the widened portion, the first and second resin sheets bulge so as to separate away from each other in a thickness direction.

11. The bag-shaped container of claim 6, further comprising an opening prevention member configured to prevent the weakly sealed portion from separating in a thickness direction.

* * * * *